(12) United States Patent
Cui et al.

(10) Patent No.: US 8,785,728 B2
(45) Date of Patent: Jul. 22, 2014

(54) AAD-12 EVENT 1606 AND RELATED TRANSGENIC SOYBEAN LINES

(75) Inventors: Yunxing C. Cui, Carmel, IN (US); Thomas Hoffman, Zionsville, IN (US); Ning Zhou, Zionsville, IN (US); Gregory J. Gilles, Alpharetta, GA (US); Terry R. Wright, Carmel, IN (US); Dawn M. Parkhurst, Avon, IN (US); Julissa Colon, West Lafayette, IN (US); Yonghe Bai, Westfield (IN)

(73) Assignee: Dow AgroSciences, LLC., Indianapolis, IN (US)

( * ) Notice: Subject to any disclaimer, the term of this patent is extended or adjusted under 35 U.S.C. 154(b) by 37 days.

(21) Appl. No.: 13/226,789

(22) Filed: Sep. 7, 2011

(65) Prior Publication Data
US 2012/0110688 A1    May 3, 2012

Related U.S. Application Data

(60) Provisional application No. 61/380,957, filed on Sep. 8, 2010.

(51) Int. Cl.
*C12N 15/82* (2006.01)
*A01H 1/00* (2006.01)
*C07H 21/04* (2006.01)

(52) U.S. Cl.
USPC .......... 800/300; 800/266; 536/24.3; 536/23.2

(58) Field of Classification Search
USPC ........................................................ 800/300
See application file for complete search history.

(56) References Cited

U.S. PATENT DOCUMENTS 5,773,695 A * 6/1998 Thompson et al. ........... 800/293
7,154,021 B2 * 12/2006 Hauge et al. .................. 800/267
7,868,149 B2 * 1/2011 Boukharov et al. .......... 536/23.1

OTHER PUBLICATIONS

Fourgoux-Nicol et al, Isolation of Rapeseed Genes Expressed Early and Specifically During Development of the Male Gametophyte, Plant Mol. Biol. (1999) 40: 857-872.*
Hohe et al, A tool for understanding homologous recombination in plants, Plant Cell Rep. (2003) 21:1135-1142.*

* cited by examiner

*Primary Examiner* — David H Kruse
*Assistant Examiner* — Mykola Kovalenko
(74) *Attorney, Agent, or Firm* — James Daly; Faere Baker Daniels LLP

(57) ABSTRACT

This invention relates to soybean event pDAB4472-1606 (Event 1606). This invention includes a novel aad-12 transformation event in soybean plants comprising a polynucleotide sequence, as described herein, inserted into a specific site within the genome of a soybean cell. This invention also relates in part to plant breeding and herbicide tolerant plants. In some embodiments, said event/polynucleotide sequence can be "stacked" with other traits, including, for example, other herbicide tolerance gene(s) and/or insect-inhibitory proteins.

16 Claims, 9 Drawing Sheets

Panel A | Panel B

| Panel A | | | | Panel B | | | |
|---|---|---|---|---|---|---|---|
| Lane | Sample | Lane | Sample | Lane | Sample | Lane | Sample |
| 1 | DIG MWM II | 10 | 1606-T3-1 | 1 | DIG MWM II | 8 | 1606-T5-5 |
|  | Maverick-2 + |  |  |  | Maverick-6 + |  |  |
| 2 | pDAB4472 | 11 | 1606-T3-3 | 2 | pDAB4472 | 9 | DIG MWM II |
| 3 | Maverick-2 | 12 | 1606-T3-7 | 3 | Maverick-6 | 10 | 1606-T6-5 |
| 4 | Maverick-6 | 13 | 1606-T3-9 | 4 | Maverick-10 | 11 | 1606-T6-6 |
| 5 | 1606-T2-9 | 14 | 1606-T4-2 | 5 | 1606-T5-1 | 12 | 1606-T6-8 |
| 6 | 1606-T2-13 | 15 | 1606-T4-7 | 6 | 1606-T5-2 | 13 | 1606-T6-10 |
| 7 | 1606-T2-14 | 16 | 1606-T4-8 | 7 | 1606-T5-4 | 14 | DIG MWM II |
| 8 | 1606-T2-15 | 17 | 1606-T4-9 |  |  |  |  |
| 9 | DIG MWM II | 18 | DIG MWM II |  |  |  |  |

Panel A                                  Panel B

| Panel A | | | | Panel B | | | |
| --- | --- | --- | --- | --- | --- | --- | --- |
| Lane | Sample | Lane | Sample | Lane | Sample | Lane | Sample |
| 1 | DIG MWM II | 10 | 1606-T3-1 | 1 | DIG MWM II | 8 | 1606-T5-5 |
| 2 | Maverick-2 + pDAB4472 | 11 | 1606-T3-3 | 2 | Maverick-6 + pDAB4472 | 9 | DIG MWM II |
| 3 | Maverick-2 | 12 | 1606-T3-7 | 3 | Maverick-6 | 10 | 1606-T6-5 |
| 4 | Maverick-5 | 13 | 1606-T3-9 | 4 | Maverick-5 | 11 | 1606-T6-6 |
| 5 | 1606-T2-9 | 14 | 1606-T4-2 | 5 | 1606-T5-1 | 12 | 1606-T6-8 |
| 6 | 1606-T2-13 | 15 | 1606-T4-7 | 6 | 1606-T5-2 | 13 | 1606-T6-10 |
| 7 | 1606-T2-14 | 16 | 1606-T4-8 | 7 | 1606-T5-4 | 14 | DIG MWM II |
| 8 | 1606-T2-15 | 17 | 1606-T4-9 | | | | |
| 9 | DIG MWM II | 18 | DIG MWM II | | | | |

| Panel A | | | | Panel B | | | |
|---|---|---|---|---|---|---|---|
| Lane | Sample | Lane | Sample | Lane | Sample | Lane | Sample |
| 1 | DIG MWM II | 10 | 1606-T3-1 | 1 | DIG MWM II | 8 | 1606-T5-5 |
| 2 | Maverick-10 + pDAB4472 | 11 | 1606-T3-3 | 2 | Maverick-10 + pDAB4472 | 9 | DIG MWM II |
| 3 | Maverick-10 | 12 | 1606-T3-7 | 3 | Maverick-10 | 10 | 1606-T6-5 |
| 4 | Maverick-6 | 13 | 1606-T3-9 | 4 | Maverick-6 | 11 | 1606-T6-6 |
| 5 | 1606-T2-9 | 14 | 1606-T4-2 | 5 | 1606-T5-1 | 12 | 1606-T6-8 |
| 6 | 1606-T2-13 | 15 | 1606-T4-7 | 6 | 1606-T5-2 | 13 | 1606-T6-10 |
| 7 | 1606-T2-14 | 16 | 1606-T4-8 | 7 | 1606-T5-4 | 14 | DIG MWM II |
| 8 | 1606-T2-15 | 17 | 1606-T4-9 | | | | |
| 9 | DIG MWM II | 18 | DIG MWM II | | | | |

Panel A                                   Panel B

| Panel A | | | | Panel B | | | |
|---|---|---|---|---|---|---|---|
| Lane | Sample | Lane | Sample | Lane | Sample | Lane | Sample |
| 1 | DIG MWM II | 10 | 1606-T3-1 | 1 | DIG MWM II | 8 | 1606-T5-5 |
| 2 | Maverick-6 + pDAB4472 | 11 | 1606-T3-3 | 2 | Maverick-2 + pDAB4472 | 9 | DIG MWM II |
| 3 | Maverick-6 | 12 | 1606-T3-7 | 3 | Maverick-2 | 10 | 1606-T6-5 |
| 4 | Maverick-5 | 13 | 1606-T3-9 | 4 | Maverick-5 | 11 | 1606-T6-6 |
| 5 | 1606-T2-9 | 14 | 1606-T4-2 | 5 | 1606-T5-1 | 12 | 1606-T6-8 |
| 6 | 1606-T2-13 | 15 | 1606-T4-7 | 6 | 1606-T5-2 | 13 | 1606-T6-10 |
| 7 | 1606-T2-14 | 16 | 1606-T4-8 | 7 | 1606-T5-4 | 14 | DIG MWM II |
| 8 | 1606-T2-15 | 17 | 1606-T4-9 | | | | |
| 9 | DIG MWM II | 18 | DIG MWM II | | | | |

US 8,785,728 B2

AAD-12 EVENT 1606 AND RELATED TRANSGENIC SOYBEAN LINES

CROSS REFERENCE TO RELATED APPLICATIONS

This application claims the benefit of U.S. Provisional Application No. 61/380,957, filed Sep. 8, 2010, the entire disclosure of which is expressly incorporated herein by reference.

BACKGROUND OF THE INVENTION

The aad-12 gene (originally from *Delftia acidovorans*) encodes the aryloxyalkanoate dioxygenase (AAD-12) protein. The trait confers tolerance to 2,4-dichlorophenoxyacetic acid, for example, and to pyridyloxyacetate herbicides. The aad-12 gene, itself, for herbicide tolerance in plants was first disclosed in WO 2007/053482.

The expression of heterologous or foreign genes in plants is influenced by where the foreign gene is inserted in the chromosome. This could be due to chromatin structure (e.g., heterochromatin) or the proximity of transcriptional regulation elements (e.g., enhancers) close to the integration site (Weising et al., *Ann. Rev. Genet* 22:421-477, 1988), for example. The same gene in the same type of transgenic plant (or other organism) can exhibit a wide variation in expression level amongst different events. There may also be differences in spatial or temporal patterns of expression. For example, differences in the relative expression of a transgene in various plant tissues may not correspond to the patterns expected from transcriptional regulatory elements present in the introduced gene construct.

Thus, large numbers of events are often created and screened in order to identify an event that expresses an introduced gene of interest to a satisfactory level for a given purpose. For commercial purposes, it is common to produce hundreds to thousands of different events and to screen those events for a single event that has desired transgene expression levels and patterns. An event that has desired levels and/or patterns of transgene expression is useful for introgressing the transgene into other genetic backgrounds by sexual outcrossing using conventional breeding methods. Progeny of such crosses maintain the transgene expression characteristics of the original transformant. This strategy is used to ensure reliable gene expression in a number of varieties that are well adapted to local growing conditions.

U.S. Patent App. 20090130071 relates to soybean event MON87701 and methods for detection. U.S. Patent Apps. 20090036308 and 20080051288 relate to soybean event 3560.4.3.5 and methods for detection. U.S. Patent App. 20080312082 relates to soybean event DP-305423-1 and methods for detection. U.S. Patent App. 20060282915 relates to soybean event MON89788 and methods for detection.

AAD-12 soybeans having the specific event disclosed herein have not previously been disclosed.

BRIEF SUMMARY OF THE INVENTION

The present invention relates in part to the AAD-12 soybean (*Glycine max*) event designated *pDAB*4472-1606 having representative seed deposited with American Type Culture Collection (ATCC) with Accession No. PTA-11028, and progeny derived thereof. The subject invention includes soybean plants comprising this event (and includes soybean plants comprising SEQ ID NO:1).

Other aspects of the invention comprise progeny plants, soybeans, seeds, and/or regenerable parts of the plants and seeds and progeny comprising soybean event pDAB4472-1606 (SEQ ID NO:1), as well as food or feed products made from any thereof (comprising SEQ ID NO:1). The invention also includes plant parts of soybean event pDAB4472-1606 that include, but are not limited to, pollen, ovule, flowers, shoots, roots, and leaves, and nuclei of vegetative cells, pollen cells, and egg cells. The invention further relates to soybean plants having tolerance to phenoxy auxinic and/or aryloxyalkanoate herbicides, novel genetic compositions of soybean event pDAB4472-1606, and aspects of agronomic performance of soybean plants comprising soybean event pDAB4472-1606.

This invention relates in part to plant breeding and herbicide tolerant plants. This invention includes a novel aad-12 transformation event in soybean plants comprising a polynucleotide sequence, as described herein, inserted into a specific site within the genome of a soybean cell.

In some embodiments, said event/polynucleotide sequence can be "stacked" with other traits, including, for example, other herbicide tolerance gene(s) and/or insect-inhibitory proteins. However, the subject invention includes plants having the single event, as described herein.

The additional traits may be stacked into the plant genome via plant breeding, re-transformation of the transgenic plant containing soybean event DAS-1606, or addition of new traits through targeted integration via homologous recombination.

Other embodiments include the excision of polynucleotide sequences which comprise soybean event DAS-1606, including for example, the pat gene expression cassette. Upon excision of a polynucleotide sequence, the modified event may be re-targeted at a specific chromosomal site wherein additional polynucleotide sequences are stacked with soybean event DAS-1606.

In one embodiment, the present invention encompasses a soybean chromosomal target site located on chromosome 8 between a BARC-030485-06876 molecular marker set forth as SEQ ID NO:27 and a BARC-038291-07245 molecular marker set forth as SEQ ID NO:28. In some embodiments, the target site comprises a heterologous nucleic acid. In some embodiments, the soybean chromosomal target site is located between the flanking sequences set forth in SEQ ID NO:1.

In one embodiment, the present invention encompasses a method of making a transgenic soybean plant comprising inserting a heterologous nucleic, acid at a position on chromosome 8 located between a BARC-030485-06876 molecular marker set forth as SEQ ID NO:27 and a BARC-038291-07245 molecular marker set forth as SEQ ID NO:28. In another embodiment, the heterologous nucleic acid is inserted on chromosome 8 between a BARC-030485-06876 molecular marker set forth as SEQ ID NO:27 and a BARC-038291-07245 molecular marker set forth as SEQ ID NO:28. In still another embodiment, the inserted heterologous nucleic acid is flanked 5' by a BARC-030485-06876 molecular marker set forth as SEQ ID NO:27 and a BARC-038291-07245 molecular marker set forth as SEQ ID NO:28.

Additionally, the subject invention provides assays for detecting the presence of the subject event in a sample (of soybeans, for example). The assays can be based on the DNA sequence of the recombinant construct, inserted into the soybean genome, and on the genomic sequences flanking the insertion site. Kits and conditions useful in conducting the assays are also provided.

Thus, the subject invention relates in part to the cloning and analysis of the DNA sequences of a whole aad-12 insert, and the border regions thereof (in transgenic soybean lines).

These sequences are unique. Based on these insert and border (and junction) sequences, event-specific primers can be and were generated. PCR analysis demonstrated that these events can be identified by analysis of the PCR amplicons generated with these event-specific primer sets. Thus, these and other related procedures can be used to uniquely identify soybean lines comprising the event of the subject invention.

BRIEF DESCRIPTION OF THE SEQUENCES

Figure 1:
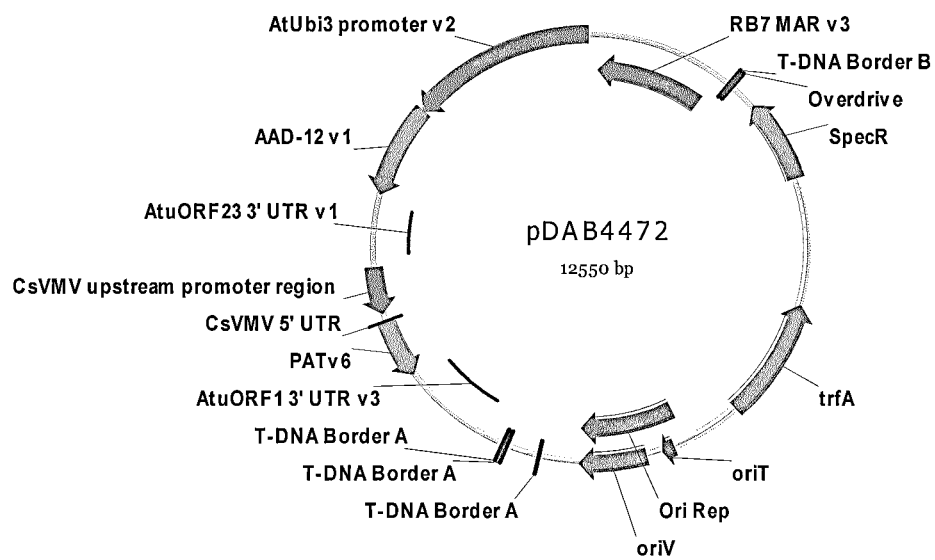
FIG. 1: Plasmid map of pDAB4472.

SEQ ID NO:1 provides insert and flanking sequences for the subject soybean Event pDAB4472-1606.

SEQ ID NOs:2-26 are primers as described herein.

SEQ ID NOs:27 and 28 are flanking SNP markers BARC-030485-06876 and BARC-038291-07245 as described herein.

SEQ ID NO:29 is representative 5' flanking sequence.

SEQ ID NO:30 is representative 3' flanking sequence.

DETAILED DESCRIPTION OF THE INVENTION

This invention includes novel transformation events of soybean plants (soybean) comprising a subject aad-12 polynucleotide sequences, as described herein, inserted into a specific site within the genome of a soybean cell.

The subject invention also provides assays for detecting the presence of the subject event in a sample. Aspects of the subject invention include methods of designing and/or producing any diagnostic nucleic acid molecules exemplified or suggested herein, particularly those based wholly or partially on the subject flanking sequences.

This invention relates in part to plant breeding and herbicide tolerant plants. In some embodiments, said polynucleotide sequence can be "stacked" with other traits (such as other herbicide tolerance gene(s) and/or gene(s) that encode insect-inhibitory proteins, for example. However, the subject invention also includes plants having a single event, as described herein.

More specifically, the subject invention relates in part to transgenic soybean event pDAB4472-1606, plant lines comprising these events, and the cloning and analysis of the DNA sequences of this insert, and/or the border regions thereof. Plant lines of the subject invention can be detected using sequences disclosed and suggested herein.

In some embodiments said polynucleotide sequences (such as the insert segment of SEQ ID NO:1) can be excised and subsequently re-targeted with additional polynucleotide sequences.

In some embodiments, this invention relates to herbicide-tolerant soybean lines, and the identification thereof. The subject invention relates in part to detecting the presence of the subject event in order to determine whether progeny of a sexual cross contain the event of interest. In addition, a method for detecting the event is included and is helpful, for example, for complying with regulations requiring the pre-market approval and labeling of foods derived from recombinant crop plants, for example. It is possible to detect the presence of the subject event by any well-known nucleic acid detection method such as polymerase chain reaction (PCR) or DNA hybridization using nucleic acid probes. Event-specific PCR assays are discussed herein. (See e.g. Windels et al. (Med. Fac. Landbouww, Univ. Gent 64/5b:459462, 1999) for another example.) Some of these examples relate to using a primer set spanning the junction between the insert and flanking DNA. More specifically, one primer included sequence from the insert and a second primer included sequence from flanking DNA.

Soybean was modified by the insertion of the aad-12 gene, derived from *Delftia acidovorans*, which encodes the aryloxyalkanoate dioxygenase (AAD-12) protein. The trait confers tolerance to 2,4-dichlorophenoxyacetic acid and pyridyloxyacetate herbicides and may be used as a selectable marker during plant transformation and in breeding nurseries.

More specifically, described herein is the AAD12 event pDAB4472-1606, and its selection and characterization for stability and expression at whole plant and molecular levels from generation to generation.

The subject synthetic gene (aad-12) used according to the subject invention was derived from *Delftia acidovorans* and encodes an enzyme capable of deactivating several herbicides with an aryloxyalkanoate moiety, including phenoxy auxin (e.g., 2,4-D, MCPA), as well as pyridyloxy auxins (e.g., fluroxypyr, triclopyr).

Both ends of event pDAB4472-1606 insertion have been sequenced and characterized. Event specific assays were developed. It has also been mapped onto the soybean genome (soybean chromosome 8); flanking SNP markers are described herein as SEQ ID NOs: 27 and 28. The event can be introgressed into further elite lines.

As alluded to above in the Background section, the introduction and integration of a transgene into a plant genome involves some random events (hence the name "event" for a given insertion that is expressed). That is, with many transformation techniques such as *Agrobacterium* transformation, the "gene gun," and WHISKERS, it is unpredictable where in the genome a transgene will become inserted. Thus, identifying the flanking plant genomic DNA on both sides of the insert can be important for identifying a plant that has a given insertion event. For example, PCR primers can be designed that generate a PCR amplicon across the junction region of the insert and the host genome. This PCR amplicon can be used to identify a unique or distinct type of insertion event.

As "events" are originally random events, as part of this disclosure at least 2500 seeds of a soybean line comprising the event have been deposited and made available to the public without restriction (but subject to patent rights), with the American Type Culture Collection (ATCC), 10801 University Boulevard, Manassas, Va., 20110. The deposit has been designated as ATCC Deposit No. PTA-11028. 100 packets (25 seeds per packet) of Glycine max seeds (AAD-12 Soybean Event pDAB4472-1606) were deposited on behalf of Dow AgroSciences LLC on Jun. 10, 2010. The deposit was tested on Jun. 29, 2010, and on that date, the seeds were viable. This deposit was made and will be maintained in accordance with and under the terms of the Budapest Treaty with respect to seed deposits for the purposes of patent procedure. The deposit will be maintained without restriction at the ATCC depository, which is a public depository, for a period of 30 years, or five years after the most recent request, or for the effective life of the patent, whichever is longer, and will be replaced if it becomes nonviable during that period.

The deposited seeds are part of the subject invention. Clearly, soybean plants can be grown from these seeds, and such plants are part of the subject invention. The subject invention also relates to DNA sequences contained in these soybean plants that are useful for detecting these plants and progeny thereof. Detection methods and kits of the subject invention can be directed to identifying any one, two, or even all three of these events, depending on the ultimate purpose of the test.

Definitions and examples are provided herein to help describe the present invention and to guide those of ordinary skill in the art to practice the invention. Unless otherwise noted, terms are to be understood according to conventional usage by those of ordinary skill in the relevant art. The nomenclature for DNA bases as set forth at 37 CFR §1.822 is used.

As used herein, the term "progeny" denotes the offspring of any generation of a parent plant which comprises AAD-12 soybean event pDAB4472-1606.

A transgenic "event" is produced by transformation of plant cells with heterologous DNA, i.e., a nucleic acid construct that includes a transgene of interest, regeneration of a population of plants resulting from the insertion of the transgene into the genome of the plant, and selection of a particular plant characterized by insertion into a particular genome location. The term "event" refers to the original transformant and progeny of the transformant that include the heterologous DNA. The term "event" also refers to progeny produced by a sexual outcross between the transformant and another variety that includes the genomic/transgene DNA. Even after repeated back-crossing to a recurrent parent, the inserted transgene DNA and flanking genomic DNA (genomic/transgene DNA) from the transformed parent is present in the progeny of the cross at the same chromosomal location. The term "event" also refers to DNA from the original transformant and progeny thereof comprising the inserted DNA and flanking genomic sequence immediately adjacent to the inserted DNA that would be expected to be transferred to a progeny that receives inserted DNA including the transgene of interest as the result of a sexual cross of one parental line that includes the inserted DNA (e.g., the original transformant and progeny resulting from selfing) and a parental line that does not contain the inserted DNA.

A "junction sequence" spans the point at which DNA inserted into the genome is linked to DNA from the soybean native genome flanking the insertion point, the identification or detection of one or the other junction sequences in a plant's genetic material being sufficient to be diagnostic for the event. Included are the DNA sequences that span the insertions in herein-described soybean events and similar lengths of flanking DNA. Specific examples of such diagnostic sequences are provided herein; however, other sequences that overlap the junctions of the insertions, or the junctions of the insertions and the genomic sequence, are also diagnostic and could be used according to the subject invention.

The subject invention relates in part to event identification using such flanking, junction, and insert sequences. Related PCR primers and amplicons are included in the invention. According to the subject invention, PCR analysis methods using amplicons that span across inserted DNA and its borders can be used to detect or identify commercialized transgenic soybean varieties or lines derived from the subject proprietary transgenic soybean lines.

The entire sequences of each of these inserts, together with portions of the respective flanking sequences, are provided herein as SEQ ID NO:1. The coordinates of the insert and flanking sequences for this event with respect to SEQ ID NO:1 (11,216 basepairs total) are listed below.

|  | 5' Flanking | Insert | 3'Flanking |
| --- | --- | --- | --- |
| residue #s (SEQ: 1): | 1-3224 | 3225-9948 | 9949-11,216 |
| length (bp): | 3224 bp | 6724 bp | 1268 bp |
|  | SEQ ID NO: 29 |  | SEQ ID NO: 30 |

These sequences (particularly the flanking sequences) are unique. Based on these insert and border sequences, event-specific primers were generated. PCR analysis demonstrated that these soybean lines can be identified in different soybean genotypes by analysis of the PCR amplicons generated with these event-specific primer sets. Thus, these and other related procedures can be used to uniquely identify these soybean lines. The sequences identified herein are unique.

Detection techniques of the subject invention are especially useful in conjunction with plant breeding, to determine which progeny plants comprise a given event, after a parent plant comprising an event of interest is crossed with another plant line in an effort to impart one or more additional traits of interest in the progeny. These PCR analysis methods benefit soybean breeding programs as well as quality control, especially for commercialized transgenic soybean seeds. PCR detection kits for these transgenic soybean lines can also now be made and used. This can also benefit product registration and product stewardship.

Furthermore, flanking soybean/genomic sequences can be used to specifically identify the genomic location of each insert. This information can be used to make molecular marker systems specific to each event. These can be used for accelerated breeding strategies and to establish linkage data.

Still further, the flanking sequence information can be used to study and characterize transgene integration processes, genomic integration site characteristics, event sorting, stability of transgenes and their flanking sequences, and gene expression (especially related to gene silencing, transgene methylation patterns, position effects, and potential expression-related elements such as MARS [matrix attachment regions], and the like).

In light of all the subject disclosure, it should be clear that the subject invention includes seeds available under ATCC Deposit No. PTA-11028. The subject invention also includes a herbicide-tolerant soybean plant grown from a seed deposited with the ATCC under accession number PTA-11028. The subject invention further includes parts of said plant, such as leaves, tissue samples, seeds produced by said plant, pollen, and the like (wherein they comprise SEQ ID NO:1).

Still further, the subject invention includes descendant and/or progeny plants of plants grown from the deposited seed, preferably a herbicide-resistant soybean plant wherein said plant has a genome comprising a detectable wild-type genomic DNA/insert DNA junction sequence as described herein. As used herein, the term "soybean" means *Glycine max* and includes all varieties thereof that can be bred with a soybean plant.

This invention further includes processes of making crosses using a plant of the subject invention as at least one parent. For example, the subject invention includes an $F_1$ hybrid plant having as one or both parents any of the plants exemplified herein. Also within the subject invention is seed produced by such $F_1$ hybrids of the subject invention. This invention includes a method for producing an $F_1$ hybrid seed by crossing an exemplified plant with a different (e.g. in-bred parent) plant and harvesting the resultant hybrid seed. The subject invention includes an exemplified plant that is either a female parent or a male parent. Characteristics of the resulting plants may be improved by careful consideration of the parent plants.

A herbicide-tolerant soybean plant of the subject invention can be bred by first sexually crossing a first parental soybean plant consisting of a soybean plant grown from seed of any one of the lines referred to herein, and a second parental soybean plant, thereby producing a plurality of first progeny plants; then selecting a first progeny plant that is resistant to a herbicide (or that possesses at least one of the events of the subject invention); selfing the first progeny plant, thereby producing a plurality of second progeny plants; and then selecting from the second progeny plants a plant that is resistant to a herbicide (or that possesses at least one of the events of the subject invention). These steps can further include the back-crossing of the first progeny plant or the second progeny plant to the second parental soybean plant or a third parental soybean plant. A soybean crop comprising soybean seeds of the subject invention, or progeny thereof, can then be planted.

It is also to be understood that two different transgenic plants can also be mated to produce offspring that contain two independently segregating, added, exogenous genes. Selfing of appropriate progeny can produce plants that are homozygous for both added, exogenous genes. Back-crossing to a parental plant and out-crossing with a non-transgenic plant are also contemplated, as is vegetative propagation. Other breeding methods commonly used for different traits and crops are known in the art. Backcross breeding has been used to transfer genes for a simply inherited, highly heritable trait into a desirable homozygous cultivar or inbred line, which is the recurrent parent. The source of the trait to be transferred is called the donor parent. The resulting plant is expected to have the attributes of the recurrent parent (e.g., cultivar) and the desirable trait transferred from the donor parent. After the initial cross, individuals possessing the phenotype of the donor parent are selected and repeatedly crossed (back-crossed) to the recurrent parent. The resulting parent is expected to have the attributes of the recurrent parent (e.g., cultivar) and the desirable trait transferred from the donor parent.

The DNA molecules of the present invention can be used as molecular markers in a marker assisted breeding (MAB) method. DNA molecules of the present invention can be used in methods (such as, AFLP markers, RFLP markers, RAPD markers, SNPs, and SSRs) that identify genetically linked agronomically useful traits, as is known in the art. The herbicide-resistance trait can be tracked in the progeny of a cross with a soybean plant of the subject invention (or progeny thereof and any other soybean cultivar or variety) using the MAB methods. The DNA molecules are markers for this trait, and MAB methods that are well known in the art can be used to track the hebicide-resistance trait(s) in soybean plants where at least one soybean line of the subject invention, or progeny thereof, was a parent or ancestor. The methods of the present invention can be used to identify any soybean variety having the subject event.

Methods of the subject invention include a method of producing a herbicide-tolerant soybean plant wherein said method comprises breeding with a plant of the subject invention. More specifically, said methods can comprise crossing two plants of the subject invention, or one plant of the subject invention and any other plant. Preferred methods further comprise selecting progeny of said cross by analyzing said progeny for an event detectable according to the subject invention. For example, the subject invention can be used to track the subject event through breeding cycles with plants comprising other desirable traits, such as agronomic traits such as those tested herein in various Examples. Plants comprising the subject event and the desired trait can be detected, identified, selected, and quickly used in further rounds of breeding, for example. The subject event/trait can also be combined through breeding, and tracked according to the subject invention, with an insect resistant trait(s) and/or with further herbicide tolerance traits. One embodiment of the latter is a plant comprising the subject event combined with a gene encoding resistance to the herbicide dicamba.

Thus, the subject invention can be combined with, for example, traits encoding glyphosate resistance (e.g., resistant plant or bacterial EPSPS, GOX, GAT), glufosinate resistance (e.g., *Pat, bar*), acetolactate synthase (ALS)-inhibiting herbicide resistance (e.g., imidazolinones [such as imazethapyr], sulfonylureas, triazolopyrimidine sulfonanilide, pyrmidinylthiobenzoates, and other chemistries [Csr1, SurA, et al.]), bromoxynil resistance (e.g., Bxn), resistance to inhibitors of HPPD (4-hydroxlphenyl-pyruvate-dioxygenase) enzyme, resistance to inhibitors of phytoene desaturase (PDS), resistance to photosystem II inhibiting herbicides (e.g., psbA), resistance to photosystem I inhibiting herbicides, resistance to protoporphyrinogen oxidase IX (PPO)-inhibiting herbicides (e.g., PPO-1), resistance to phenylurea herbicides (e.g., CYP76B1), dicamba-degrading enzymes (see, e.g., US 20030135879), and others could be stacked alone or in multiple combinations to provide the ability to effectively control or prevent weed shifts and/or resistance to any herbicide of the aforementioned classes.

Regarding additional herbicides, some additional preferred ALS (also known as AHAS) inhibitors include the triazolopyrimidine sulfonanilides (such as cloransulam-methyl, diclosulam, florasulam, flumetsulam, metosulam, and penoxsulam), pyrimidinylthiobenzoates (such as bispyribac and pyrithiobac), and flucarbazone. Some preferred HPPD inhibitors include mesotrione, isoxaflutole, and sulcotrione. Some preferred PPO inhibitors include flumiclorac, flumioxazin, flufenpyr, pyraflufen, fluthiacet, butafenacil, carfentrazone, sulfentrazone, and the diphenylethers (such as acifluorfen, fomesafen, lactofen, and oxyfluorfen).

Additionally, aad-12 alone or stacked with one or more additional HTC traits can be stacked with one or more additional input (e.g., insect resistance, fungal resistance, or stress tolerance, et al.) or output (e.g., increased yield, improved oil profile, improved fiber quality, et al.) traits. Thus, the subject invention can be used to provide a complete agronomic package of improved crop quality with the ability to flexibly and cost effectively control any number of agronomic pests.

Methods to integrate a polynucleotide sequence within a specific chromosomal site of a plant cell via homologous recombination have been described within the art. For instance, site specific integration as described in US Patent Application Publication No. 2009/0111188 A1, herein incorporated by reference, describes the use of recombinases or integrases to mediate the introduction of a donor polynucleotide sequence into a chromosomal target. In addition, International Patent Application No. WO 2008/021207, herein incorporated by reference, describes zinc finger mediated-homologous recombination to integrate one or more donor polynucleotide sequences within specific locations of the genome. The use of recombinases such as FLP/FRT as described in U.S. Pat. No. 6,720,475, herein incorporated by reference, or CRE/LOX as described in U.S. Pat. No. 5,658,772, herein incorporated by reference, can be utilized to integrate a polynucleotide sequence into a specific chromosomal site. Finally the use of meganucleases for targeting donor polynucleotides into a specific chromosomal location was described in Puchta et al., PNAS USA 93 (1996) pp. 5055-5060).

Other various methods for site specific integration within plant cells are generally known and applicable (Kumar et al., *Trends in Plant Sci.* 6(4) (2001) pp. 155-159). Furthermore, site-specific recombination systems which have been identified in several prokaryotic and lower eukaryotic organisms may be applied to use in plants. Examples of such systems include, but are not limited too; the R/RS recombinase system from the pSR1 plasmid of the yeast *Zygosaccharomyces rouxii* (Araki et al. (1985) J. Mol. Biol. 182: 191-203), and the Gin/gix system of phage Mu (Maeser and Kahlmann (1991) Mol. Gen. Genet. 230: 170-176).

In some embodiments of the present invention, it can be desirable to integrate or stack a new transgene(s) in proximity to an existing transgenic event. The transgenic event can be considered a preferred genomic locus which was selected based on unique characteristics such as single insertion site, normal Mendelian segregation and stable expression, and a superior combination of efficacy, including herbicide tolerance and agronomic performance in and across multiple environmental locations. The newly integrated transgenes should maintain the transgene expression characteristics of the existing transformants. Moreover, the development of assays for the detection and confirmation of the newly integrated event would be overcome as the genomic flanking sequences and chromosomal location of the newly integrated event are already identified. Finally, the integration of a new transgene into a specific chromosomal location which is linked to an existing transgene would expedite the introgression of the transgenes into other genetic backgrounds by sexual outcrossing using conventional breeding methods.

In some embodiments of the present invention, it can be desirable to excise polynucleotide sequences from a transgenic event. For instance transgene excision as described in Provisional U.S. Patent Application No. 61/297,628, herein incorporated by reference, describes the use of zinc finger nucleases to remove a polynucleotide sequence, consisting of a gene expression cassette, from a chromosomally integrated transgenic event. The polynucleotide sequence which is removed can be a selectable marker. Upon excision and removal of a polynucleotide sequence the modified transgenic event can be retargeted by the insertion of a polynucleotide sequence. The excision of a polynucleotide sequence and subsequent retargeting of the modified transgenic event provides advantages such as re-use of a selectable marker or the ability to overcome unintended changes to the plant transcriptome which results from the expression of specific genes.

The subject invention discloses herein a specific site on chromosome 8 in the soybean genome that is excellent for insertion of heterologous nucleic acids. Also disclosed is a 5' molecular marker (BARC-030485-06876) and a 3' molecular marker (BARC-038291-07245) useful in identifying the location of a targeting site on chromosome 8. Thus, the subject invention provides methods to introduce heterologous nucleic acids of interest into this pre-established target site or in the vicinity of this target site. The subject invention also encompasses a soybean seed and/or a soybean plant comprising any heterologous nucleotide sequence inserted at the disclosed target site or in the general vicinity of such site. One option to accomplish such targeted integration is to excise and/or substitute a different insert in place of the pat expression cassette exemplified herein. In this general regard, targeted homologous recombination, for example and without limitation, can be used according to the subject invention.

As used herein gene, event or trait "stacking" is combining desired traits into one transgenic line. Plant breeders stack transgenic traits by making crosses between parents that each have a desired trait and then identifying offspring that have both of these desired traits. Another way to stack genes is by transferring two or more genes into the cell nucleus of a plant at the same time during transformation. Another way to stack genes is by re-transforming a transgenic plant with another gene of interest. For example, gene stacking can be used to combine two or more different traits, including, for example, two or more different insect traits, insect resistance trait(s) and disease resistance trait(s), two or more herbicide resistance traits, and/or insect resistance trait(s) and herbicide resistant trait(s). The use of a selectable marker in addition to a gene of interest can also be considered gene stacking.

"Homologous recombination" refers to a reaction between any pair of nucleotide sequences having corresponding sites containing a similar nucleotide sequence through which the two nucleotide sequences can interact (recombine) to form a new, recombinant DNA sequence. The sites of similar nucleotide sequence are each referred to herein as a "homology sequence." Generally, the frequency of homologous recombination increases as the length of the homology sequence increases. Thus, while homologous recombination can occur between two nucleotide sequences that are less than identical, the recombination frequency (or efficiency) declines as the divergence between the two sequences increases. Recombination may be accomplished using one homology sequence on each of the donor and target molecules, thereby generating a "single-crossover" recombination product. Alternatively, two homology sequences may be placed on each of the target and donor nucleotide sequences. Recombination between two homology sequences on the donor with two homology sequences on the target generates a "double-crossover" recombination product. If the homology sequences on the donor molecule flank a sequence that is to be manipulated (e.g., a sequence of interest), the double-crossover recombination with the target molecule will result in a recombination product wherein the sequence of interest replaces a DNA sequence that was originally between the homology sequences on the target molecule. The exchange of DNA sequence between the target and donor through a double-crossover recombination event is termed "sequence replacement."

The subject AAD-12 enzyme enables transgenic expression resulting in tolerance to combinations of herbicides that would control nearly all broadleaf and grass weeds. AAD-12 can serve as an excellent herbicide tolerant crop (HTC) trait to stack with other HTC traits (e.g., glyphosate resistance, glufosinate resistance, imidazolinone resistance, bromoxynil resistance, et al.), and insect resistance traits (Cry1F, Cry1Ab, Cry1Ac, Cry 34/45, et al.) for example. Additionally, AAD-12 can serve as a selectable marker to aid in selection of primary transformants of plants genetically engineered with a second gene or group of genes.

HTC traits of the subject invention can be used in novel combinations with other HTC traits (including but not limited to glyphosate tolerance). These combinations of traits give rise to novel methods of controlling weed (and like) species, due to the newly acquired resistance or inherent tolerance to herbicides (e.g., glyphosate). Thus, in addition to the HTC traits, novel methods for controlling weeds using herbicides, for which herbicide tolerance was created by said enzyme in transgenic crops, are within the scope of the invention.

Additionally, glyphosate tolerant crops grown worldwide are prevalent. Many times in rotation with other glyphosate tolerant crops, control of glyphosate-resistant volunteers may be difficult in rotational crops. Thus, the use of the subject transgenic traits, stacked or transformed individually into crops, provides a tool for controlling other HTC volunteer crops.

A preferred plant, or a seed, of the subject invention comprises in its genome the insert sequences, as identified herein, together with at least 20-500 or more contiguous flanking nucleotides on both sides of the insert, as identified herein. Unless indicated otherwise, reference to flanking sequences refers to those identified with respect to SEQ ID NO:1 (see the table above). Again, SEQ ID NO:1 includes the heterologous DNA inserted in the original transformant and illustrative flanking genomic sequences immediately adjacent to the inserted DNA. All or part of these flanking sequences could be expected to be transferred to progeny that receives the inserted DNA as a result of a sexual cross of a parental line that includes the event.

The subject invention includes tissue cultures of regenerable cells of a plant of the subject invention. Also included is a plant regenerated from such tissue culture, particularly where said plant is capable of expressing all the morphological and physiological properties of an exemplified variety. Preferred plants of the subject invention have all the physiological and morphological characteristics of a plant grown from the deposited seed. This invention further comprises progeny of such seed and seed possessing the quality traits of interest.

Manipulations (such as mutation, further transfection, and further breeding) of plants or seeds, or parts thereof, may lead to the creation of what may be termed "essentially derived" varieties. The International Union for the Protection of New Varieties of Plants (UPOV) has provided the following guideline for determining if a variety has been essentially derived from a protected variety:

[A] variety shall be deemed to be essentially derived from another variety ("the initial variety") when
(i) it is predominantly derived from the initial variety, or from a variety that is itself predominantly derived from the initial variety, while retaining the expression of the essential characteristics that result from the genotype or combination of genotypes of the initial variety;
(ii) it is clearly distinguishable from the initial variety; and
(iii) except for the differences which result from the act of derivation, it conforms to the initial variety in the expression of the essential characteristics that result from the genotype or combination of genotypes of the initial variety.

UPOV, Sixth Meeting with International Organizations, Geneva, Oct. 30, 1992; document prepared by the Office of the Union.

As used herein, a "line" is a group of plants that display little or no genetic variation between individuals for at least one trait. Such lines may be created by several generations of self-pollination and selection, or vegetative propagation from a single parent using tissue or cell culture techniques.

As used herein, the terms "cultivar" and "variety" are synonymous and refer to a line which is used for commercial production.

"Stability" or "stable" means that with respect to the given component, the component is maintained from generation to generation and, preferably, at least three generations at substantially the same level, e.g., preferably ±15%, more preferably ±10%, most preferably ±5%. The stability may be affected by temperature, location, stress and the time of planting. Comparison of subsequent generations under field conditions should produce the component in a similar manner.

"Commercial Utility" is defined as having good plant vigor and high fertility, such that the crop can be produced by farmers using conventional farming equipment, and the oil with the described components can be extracted from the seed using conventional crushing and extraction equipment. To be commercially useful, the yield, as measured by seed weight, oil content, and total oil produced per acre, is within 15% of the average yield of an otherwise comparable commercial canola variety without the premium value traits grown in the same region.

"Agronomically elite" means that a line has desirable agronomic characteristics such as yield, maturity, disease resistance, and the like, in addition to the herbicide tolerance due to the subject event(s). Agronomic traits, taken individually or in any combination, as set forth in Examples, below, in a plant comprising an event of the subject invention, are within the scope of the subject invention. Any and all of these agronomic characteristics and data points can be used to identify such plants, either as a point or at either end or both ends of a range of characteristics used to define such plants.

As one skilled in the art will recognize in light of this disclosure, preferred embodiments of detection kits, for example, can include probes and/or primers directed to and/or comprising "junction sequences" or "transition sequences" (where the soybean genomic flanking sequence meets the insert sequence). For example, this includes a polynucleotide probes, primers, and/or amplicons designed to identify one or both junction sequences (where the insert meets the flanking sequence), as indicated in the Table above. One common design is to have one primer that hybridizes in the flanking region, and one primer that hybridizes in the insert. Such primers are often each about at least ~15 residues in length. With this arrangement, the primers can be used to generate/amplify a detectable amplicon that indicates the presence of an event of the subject invention. These primers can be used to generate an amplicon that spans (and includes) a junction sequence as indicated above.

The primer(s) "touching down" in the flanking sequence is typically not designed to hybridize beyond about 200 bases or so beyond the junction. Thus, typical flanking primers would be designed to comprise at least 15 residues of either strand within 200 bases into the flanking sequences from the beginning of the insert. That is, primers comprising a sequence of an appropriate size from (or hybridizing to) residues ~3024-3224 and/or ~9949-10,148 of SEQ ID NO:1 are within the scope of the subject invention. Insert primers can likewise be designed anywhere on the insert, but residues ~3225-3425 and ~9748-9948, can be used, for example, non-exclusively for such primer design.

One skilled in the art will also recognize that primers and probes can be designed to hybridize, under a range of standard hybridization and/or PCR conditions, to a segment of SEQ ID NO:1 (or the complement), and complements thereof, wherein the primer or probe is not perfectly complementary to the exemplified sequence. That is, some degree of mismatch can be tolerated. For an approximately 20 nucleotide primer, for example, typically one or two or so nucleotides do not need to bind with the opposite strand if the mismatched base is internal or on the end of the primer that is opposite the amplicon. Various appropriate hybridization conditions are provided below. Synthetic nucleotide analogs, such as inosine, can also be used in probes. Peptide nucleic acid (PNA) probes, as well as DNA and RNA probes, can also be used. What is important is that such probes and primers are diagnostic for (able to uniquely identify and distinguish) the presence of an event of the subject invention.

It should be noted that errors in PCR amplification can occur which might result in minor sequencing errors, for example. That is, unless otherwise indicated, the sequences listed herein were determined by generating long amplicons from soybean genomic DNAs, and then cloning and sequencing the amplicons. It is not unusual to find slight differences and minor discrepancies in sequences generated and determined in this manner, given the many rounds of amplification that are necessary to generate enough amplicon for sequencing from genomic DNAs. One skilled in the art should recognize and be put on notice that any adjustments needed due to these types of common sequencing errors or discrepancies are within the scope of the subject invention.

It should also be noted that it is not uncommon for some genomic sequence to be deleted, for example, when a sequence is inserted during the creation of an event. Thus, some differences can also appear between the subject flanking sequences and genomic sequences listed in GENBANK, for example.

Components of the "insert" are illustrated in the Figures and are discussed in more detail below in the Examples. The DNA polynucleotide sequences of these components, or fragments thereof, can be used as DNA primers or probes in the methods of the present invention.

In some embodiments of the invention, compositions and methods are provided for detecting the presence of the transgene/genomic insertion region, in plants and seeds and the like, from a soybean plant. DNA sequences are provided that comprise the subject transgene/genomic insertion region junction sequence provided herein (between residues 3224-3225 and 9948-9949 of SEQ ID NO:1), segments thereof, and complements of the exemplified sequences and any segments thereof. The insertion region junction sequence spans the junction between heterologous DNA inserted into the genome and the DNA from the soybean cell flanking the insertion site. Such sequences can be diagnostic for the given event.

Based on these insert and border sequences, event-specific primers can be generated. PCR analysis demonstrated that soybean lines of the subject invention can be identified in different soybean genotypes by analysis of the PCR amplicons generated with these event-specific primer sets. These and other related procedures can be used to uniquely identify these soybean lines. Thus, PCR amplicons derived from such primer pairs are unique and can be used to identify these soybean lines.

In some embodiments, DNA sequences that comprise a contiguous fragment of the novel transgene/genomic insertion region are an aspect of this invention. Included are DNA sequences that comprise a sufficient length of polynucleotides of transgene insert sequence and a sufficient length of polynucleotides of soybean genomic sequence from one or more of the three aforementioned soybean plants and/or sequences that are useful as primer sequences for the production of an amplicon product diagnostic for one or more of these soybean plants.

Related embodiments pertain to DNA sequences that comprise at least 2, 3, 4, 5, 6, 7, 8, 9, 10, 11, 12, 13, 14, 15, 16, 17, 18, 19, 20, 21, 22, 23, 24, 25, or more contiguous nucleotides of a transgene portion of a DNA sequence identified herein (such as SEQ ID NO:1 and segments thereof), or complements thereof, and a similar length of flanking soybean DNA sequence from these sequences, or complements thereof. Such sequences are useful as DNA primers in DNA amplification methods. The amplicons produced using these primers are diagnostic for any of the soybean events referred to herein. Therefore, the invention also includes the amplicons produced by such DNA primers and homologous primers.

This invention also includes methods of detecting the presence of DNA, in a sample, that corresponds to the soybean event referred to herein. Such methods can comprise: (a) contacting the sample comprising DNA with a primer set that, when used in a nucleic acid amplification reaction with DNA from at least one of these soybean events, produces an amplicon that is diagnostic for said event(s); (b) performing a nucleic acid amplification reaction, thereby producing the amplicon; and (c) detecting the amplicon.

Further detection methods of the subject invention include a method of detecting the presence of a DNA, in a sample, corresponding to said event, wherein said method comprises: (a) contacting the sample comprising DNA with a probe that hybridizes under stringent hybridization conditions with DNA from at least one of said soybean events and which does not hybridize under the stringent hybridization conditions with a control soybean plant (non-event-of-interest DNA); (b) subjecting the sample and probe to stringent hybridization conditions; and (c) detecting hybridization of the probe to the DNA.

In still further embodiments, the subject invention includes methods of producing a soybean plant comprising the aad-12 event of the subject invention, wherein said method comprises the steps of: (a) sexually crossing a first parental soybean line (comprising an expression cassettes of the present invention, which confers said herbicideresistance trait to plants of said line) and a second parental soybean line (that lacks this herbicide tolerance trait) thereby producing a plurality of progeny plants; and (b) selecting a progeny plant by the use of molecular markers. Such methods may optionally comprise the further step of back-crossing the progeny plant to the second parental soybean line to producing a true-breeding soybean plant that comprises said herbicide tolerance trait.

According to another aspect of the invention, methods of determining the zygosity of progeny of a cross with said event is provided. Said methods can comprise contacting a sample, comprising soybean DNA, with a primer set of the subject invention. Said primers, when used in a nucleic-acid amplification reaction with genomic DNA from at least one of said soybean events, produces a first amplicon that is diagnostic for at least one of said soybean events. Such methods further comprise performing a nucleic acid amplification reaction, thereby producing the first amplicon; detecting the first amplicon; and contacting the sample comprising soybean DNA with said primer set (said primer set, when used in a nucleic-acid amplification reaction with genomic DNA from soybean plants, produces a second amplicon comprising the native soybean genomic DNA homologous to the soybean genomic region; and performing a nucleic acid amplification reaction, thereby producing the second amplicon. The methods further comprise detecting the second amplicon, and comparing the first and second amplicons in a sample, wherein the presence of both amplicons indicates that the sample is heterozygous for the transgene insertion.

DNA detection kits can be developed using the compositions disclosed herein and methods well known in the art of DNA detection. The kits are useful for identification of the subject soybean event DNA in a sample and can be applied to methods for breeding soybean plants containing this DNA. The kits contain DNA sequences homologous or complementary to the amplicons, for example, disclosed herein, or to DNA sequences homologous or complementary to DNA contained in the transgene genetic elements of the subject events. These DNA sequences can be used in DNA amplification reactions or as probes in a DNA hybridization method. The kits may also contain the reagents and materials necessary for the performance of the detection method.

A "probe" is an isolated nucleic acid molecule to which is attached a conventional detectable label or reporter molecule (such as a radioactive isotope, ligand, chemiluminescent agent, or enzyme). Such a probe is complementary to a strand of a target nucleic acid, in the case of the present invention, to a strand of genomic DNA from one of said soybean events, whether from a soybean plant or from a sample that includes DNA from the event. Probes according to the present invention include not only deoxyribonucleic or ribonucleic acids but also polyamides and other probe materials that bind specifically to a target DNA sequence and can be used to detect the presence of that target DNA sequence.

"Primers" are isolated/synthesized nucleic acids that are annealed to a complementary target DNA strand by nucleic acid hybridization to form a hybrid between the primer and the target DNA strand, then extended along the target DNA strand by a polymerase, e.g., a DNA polymerase. Primer pairs of the present invention refer to their use for amplification of a target nucleic acid sequence, e.g., by the polymerase chain reaction (PCR) or other conventional nucleic-acid amplification methods.

Probes and primers are generally 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, or 500 polynucleotides or more in length. Such probes and primers hybridize specifically to a target sequence under high stringency hybridization conditions. Preferably, probes and primers according to the present invention have complete sequence similarity with the target sequence, although probes differing from the target sequence and that retain the ability to hybridize to target sequences may be designed by conventional methods.

Methods for preparing and using probes and primers are described, for example, in Molecular Cloning: A Laboratory Manual, 2nd ed., vol. 1-3, ed. Sambrook et al., Cold Spring Harbor Laboratory Press, Cold Spring Harbor, N.Y., 1989. PCR-primer pairs can be derived from a known sequence, for example, by using computer programs intended for that purpose.

Primers and probes based on the flanking DNA and insert sequences disclosed herein can be used to confirm (and, if necessary, to correct) the disclosed sequences by conventional methods, e.g., by re-cloning and sequencing such sequences.

The nucleic acid probes and primers of the present invention hybridize under stringent conditions to a target DNA sequence. Any conventional nucleic acid hybridization or amplification method can be used to identify the presence of DNA from a transgenic event in a sample. Nucleic acid molecules or fragments thereof are capable of specifically hybridizing to other nucleic acid molecules under certain circumstances. As used herein, two nucleic acid molecules are said to be capable of specifically hybridizing to one another if the two molecules are capable of forming an anti-parallel, double-stranded nucleic acid structure. A nucleic acid molecule is said to be the "complement" of another nucleic acid molecule if they exhibit complete complementarity. As used herein, molecules are said to exhibit "complete complementarity" when every nucleotide of one of the molecules is complementary to a nucleotide of the other. Two molecules are said to be "minimally complementary" if they can hybridize to one another with sufficient stability to permit them to remain annealed to one another under at least conventional "low-stringency" conditions. Similarly, the molecules are said to be "complementary" if they can hybridize to one another with sufficient stability to permit them to remain annealed to one another under conventional "high-stringency" conditions. Conventional stringency conditions are described by Sambrook et al., 1989. Departures from complete complementarity are therefore permissible, as long as such departures do not completely preclude the capacity of the molecules to form a double-stranded structure. In order for a nucleic acid molecule to serve as a primer or probe it need only be sufficiently complementary in sequence to be able to form a stable double-stranded structure under the particular solvent and salt concentrations employed.

As used herein, a substantially homologous sequence is a nucleic acid sequence that will specifically hybridize to the complement of the nucleic acid sequence to which it is being compared under high stringency conditions. The term "stringent conditions" is functionally defined with regard to the hybridization of a nucleic-acid probe to a target nucleic acid (i.e., to a particular nucleic-acid sequence of interest) by the specific hybridization procedure discussed in Sambrook et al., 1989, at 9.52-9.55. See also, Sambrook et al., 1989 at 9.47-9.52 and 9.56-9.58. Accordingly, the nucleotide sequences of the invention may be used for their ability to selectively form duplex molecules with complementary stretches of DNA fragments.

Depending on the application envisioned, one can use varying conditions of hybridization to achieve varying degrees of selectivity of probe towards target sequence. For applications requiring high selectivity, one will typically employ relatively stringent conditions to form the hybrids, e.g., one will select relatively low salt and/or high temperature conditions, such as provided by about 0.02 M to about 0.15 M NaCl at temperatures of about 50° C. to about 70° C. Stringent conditions, for example, could involve washing the hybridization filter at least twice with high-stringency wash buffer (0.2×SSC, 0.1% SDS, 65° C.). Appropriate stringency conditions which promote DNA hybridization, for example, 6.0× sodium chloride/sodium citrate (SSC) at about 45° C., followed by a wash of 2.0×SSC at 50° C. are known to those skilled in the art. For example, the salt concentration in the wash step can be selected from a low stringency of about 2.0×SSC at 50° C. to a high stringency of about 0.2×SSC at 50° C. In addition, the temperature in the wash step can be increased from low stringency conditions at room temperature, about 22° C., to high stringency conditions at about 65° C. Both temperature and salt may be varied, or either the temperature or the salt concentration may be held constant while the other variable is changed. Such selective conditions tolerate little, if any, mismatch between the probe and the template or target strand. Detection of DNA sequences via hybridization is well-known to those of skill in the art, and the teachings of U.S. Pat. Nos. 4,965,188 and 5,176,995 are exemplary of the methods of hybridization analyses.

In a particularly preferred embodiment, a nucleic acid of the present invention will specifically hybridize to one or more of the primers (or amplicons or other sequences) exemplified or suggested herein, including complements and fragments thereof, under high stringency conditions. In one aspect of the present invention, a marker nucleic acid molecule of the present invention has the nucleic acid sequence as set forth herein in one of the exemplified sequences, or complements and/or fragments thereof.

In another aspect of the present invention, a marker nucleic acid molecule of the present invention shares between 80% and 100% or 90% and 100% sequence identity with such nucleic acid sequences. In a further aspect of the present invention, a marker nucleic acid molecule of the present invention shares between 95% and 100% sequence identity with such sequence. Such sequences may be used as markers in plant breeding methods to identify the progeny of genetic crosses. The hybridization of the probe to the target DNA molecule can be detected by any number of methods known to those skilled in the art, these can include, but are not limited to, fluorescent tags, radioactive tags, antibody based tags, and chemiluminescent tags.

Regarding the amplification of a target nucleic acid sequence (e.g., by PCR) using a particular amplification primer pair, "stringent conditions" are conditions that permit the primer pair to hybridize only to the target nucleic-acid sequence to which a primer having the corresponding wild-type sequence (or its complement) would bind and preferably to produce a unique amplification product, the amplicon.

The term "specific for (a target sequence)" indicates that a probe or primer hybridizes under stringent hybridization conditions only to the target sequence in a sample comprising the target sequence.

As used herein, "amplified DNA" or "amplicon" refers to the product of nucleic-acid amplification of a target nucleic acid sequence that is part of a nucleic acid template. For example, to determine whether the soybean plant resulting from a sexual cross contains transgenic event genomic DNA from the soybean plant of the present invention, DNA extracted from a soybean plant tissue sample may be subjected to nucleic acid amplification method using a primer pair that includes a primer derived from flanking sequence in the genome of the plant adjacent to the insertion site of inserted heterologous DNA, and a second primer derived from the inserted heterologous DNA to produce an amplicon that is diagnostic for the presence of the event DNA. The amplicon is of a length and has a sequence that is also diagnostic for the event. The amplicon may range in length from the combined length of the primer pairs plus one nucleotide base pair, and/or the combined length of the primer pairs plus about 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, or 500, 750, 1000, 1250, 1500, 1750, 2000, or more nucleotide base pairs (plus or minus any of the increments listed above). Alternatively, a primer pair can be derived from flanking sequence on both sides of the inserted DNA so as to produce an amplicon that includes the entire insert nucleotide sequence. A member of a primer pair derived from the plant genomic sequence may be located a distance from the inserted DNA sequence. This distance can range from one nucleotide base pair up to about twenty thousand nucleotide base pairs. The use of the term "amplicon" specifically excludes primer dimers that may be formed in the DNA thermal amplification reaction.

Nucleic-acid amplification can be accomplished by any of the various nucleic-acid amplification methods known in the art, including the polymerase chain reaction (PCR). A variety of amplification methods are known in the art and are described, inter alia, in U.S. Pat. No. 4,683,195 and U.S. Pat. No. 4,683,202. PCR amplification methods have been developed to amplify up to 22 kb of genomic DNA. These methods as well as other methods known in the art of DNA amplification may be used in the practice of the present invention. The sequence of the heterologous transgene DNA insert or flanking genomic sequence from a subject soybean event can be verified (and corrected if necessary) by amplifying such sequences from the event using primers derived from the sequences provided herein followed by standard DNA sequencing of the PCR amplicon or of the cloned DNA.

The amplicon produced by these methods may be detected by a plurality of techniques. Agarose gel electrophoresis and staining with ethidium bromide is a common well known method of detecting DNA amplicons. Another such method is Genetic Bit Analysis where an DNA oligonucleotide is designed which overlaps both the adjacent flanking genomic DNA sequence and the inserted DNA sequence. The oligonucleotide is immobilized in wells of a microwell plate. Following PCR of the region of interest (using one primer in the inserted sequence and one in the adjacent flanking genomic sequence), a single-stranded PCR product can be hybridized to the immobilized oligonucleotide and serve as a template for a single base extension reaction using a DNA polymerase and labelled ddNTPs specific for the expected next base. Readout may be fluorescent or ELISA-based. A signal indicates presence of the insert/flanking sequence due to successful amplification, hybridization, and single base extension.

Another method is the Pyrosequencing technique as described by Winge (Innov. Pharma. Tech. 00:18-24, 2000). In this method an oligonucleotide is designed that overlaps the adjacent genomic DNA and insert DNA junction. The oligonucleotide is hybridized to single-stranded PCR product from the region of interest (one primer in the inserted sequence and one in the flanking genomic sequence) and incubated in the presence of a DNA polymerase, ATP, sulfurylase, luciferase, apyrase, adenosine 5' phosphosulfate and luciferin. DNTPs are added individually and the incorporation results in a light signal that is measured. A light signal indicates the presence of the transgene insert/flanking sequence due to successful amplification, hybridization, and single or multi-base extension.

Fluorescence Polarization is another method that can be used to detect an amplicon of the present invention. Following this method, an oligonucleotide is designed which overlaps the genomic flanking and inserted DNA junction. The oligonucleotide is hybridized to single-stranded PCR product from the region of interest (one primer in the inserted DNA and one in the flanking genomic DNA sequence) and incubated in the presence of a DNA polymerase and a fluorescent-labeled ddNTP. Single base extension results in incorporation of the ddNTP. Incorporation can be measured as a change in polarization using a fluorometer. A change in polarization indicates the presence of the transgene insert/flanking sequence due to successful amplification, hybridization, and single base extension.

TAQMAN (PE Applied Biosystems, Foster City, Calif.) is a method of detecting and quantifying the presence of a DNA sequence. Briefly, a FRET oligonucleotide probe is designed that overlaps the genomic flanking and insert DNA junction. The FRET probe and PCR primers (one primer in the insert DNA sequence and one in the flanking genomic sequence) are cycled in the presence of a thermostable polymerase and dNTPs. During specific amplification, Taq DNA polymerase cleans and releases the fluorescent moiety away from the quenching moiety on the FRET probe. A fluorescent signal indicates the presence of the flanking/transgene insert sequence due to successful amplification and hybridization.

Molecular Beacons have been described for use in sequence detection. Briefly, a FRET oligonucleotide probe is designed that overlaps the flanking genomic and insert DNA junction. The unique structure of the FRET probe results in it containing secondary structure that keeps the fluorescent and quenching moieties in close proximity. The FRET probe and PCR primers (one primer in the insert DNA sequence and one in the flanking genomic sequence) are cycled in the presence of a thermostable polymerase and dNTPs. Following successful PCR amplification, hybridization of the FRET probe to the target sequence results in the removal of the probe secondary structure and spatial separation of the fluorescent and quenching moieties. A fluorescent signal results. A fluorescent signal indicates the presence of the flanking genomic/transgene insert sequence due to successful amplification and hybridization.

Having disclosed a location in the soybean genome that is excellent for an insertion, the subject invention also comprises a soybean seed and/or a soybean plant comprising at least one non-aad12 insert in the general vicinity of this genomic location. One option is to substitute a different insert in place of the aad-12 insert exemplified herein. In these general regards, targeted homologous recombination, for example, can be used according to the subject invention. This type of technology is the subject of, for example, WO 03/080809 A2 and the corresponding published U.S. application (US 20030232410). Thus, the subject invention includes plants and plant cells comprising a heterologous insert (in place of or with multi-copies of aad-12), flanked by all or a recognizable part of the flanking sequences identified herein (e.g. residues 1-3224 and 9949-11,216 of SEQ ID NO:1). An additional copy (or additional copies) of an aad-12 gene could also be targeted for insertion in this/these manner(s).

All patents, patent applications, provisional applications, and publications referred to or cited herein are incorporated by reference in their entirety to the extent they are not inconsistent with the explicit teachings of this specification.

The following examples are included to illustrate procedures for practicing the invention and to demonstrate certain preferred embodiments of the invention. These examples should not be construed as limiting. It should be appreciated by those of skill in the art that the techniques disclosed in the following examples represent specific approaches used to illustrate preferred modes for its practice. However, those of skill in the art should, in light of the present disclosure, appreciate that many changes can be made in these specific embodiments while still obtaining like or similar results without departing from the spirit and scope of the invention.

Unless otherwise indicated, all percentages are by weight and all solvent mixture proportions are by volume unless otherwise noted.

The following abbreviations are used unless otherwise indicated.

AAD-12 aryloxyalkanoate dioxygenase-1
bb base pair
° C. degrees Celcius
DNA deoxyribonucleic acid
DIG digoxigenin
EDTA ethylenediaminetetraacetic acid
kb kilobase
μg micro gram
μL microliter
mL milliliter
M molar mass
OLP overlapping probe
PCR polymerase chain reaction
PTU plant transcription unit SDS sodium dodecyl sulfate
SOP standard operating procedure
SSC a buffer solution containing a mixture of sodium chloride and sodium citrate, pH 7.0
TBE a buffer solution containing a mixture of Tris base, boric acid and EDTA,
pH 8.3
V volts

EXAMPLES

Example 1

Transformation and Selection of the aad-12 Soybean Event DAS-1606

Transgenic soybean (*Glycine max*) event DAS-1606 (also described as soybean event pDAB4472-1606) was generated through *Agrobacterium*-mediated transformation of soybean cotyledonary node explants. The disarmed *Agrobacterium* strain EHA101 (Hood et al., 2006), carrying the binary vector pDAB4472 (FIG. 1) containing the selectable marker (pat) and the gene of interest (aad-12) within the T-strand DNA region, was used to initiate transformation.

*Agrobacterium-mediated transformation was carried out using a modified procedure of Zeng et al. (2004). Briefly, soybean seeds (cv Maverick) were germinated on basal media and cotyledonary nodes were isolated and infected with Agrobacterium.* Shoot initiation, shoot elongation, and rooting media were supplemented with cefotaxime, timentin and vancomycin for removal of *Agrobacterium*. Glufosinate selection was employed to inhibit the growth of non-transformed shoots. Selected shoots were transferred to rooting medium for root development and then transferred to soil mix for acclimatization of plantlets.

Terminal leaflets of selected plantlets were leaf painted with glufosinate to screen for putative transformants. The screened plantlets were transferred to the greenhouse, allowed to acclimate and then leaf-painted with glufosinate to reconfirm tolerance and deemed to be putative transformants. The screened plants were sampled and molecular analyses for the confirmation of the selectable marker gene and/or the gene of interest were carried out. $T_0$ plants were allowed to self fertilize in the greenhouse to give rise to $T_1$ seed.

This event, soybean event pDAB4472-1606, was generated from an independent transformed isolate. The $T_1$ plants were backcrossed and introgressed into elite germplasm (Maverick) over subsequent generations. The event was selected based on its unique characteristics such as single insertion site, normal Mendelian segregation and stable expression, and a superior combination of efficacy, including herbicide tolerance and agronomic performance in across multiple environmental locations. The following examples contain the data which were used to characterize soybean event pDAB4472-1606.

Example 2

Soybean Event DAS-1606 Characterization via Southern Blot

Southern blot analysis was used to establish the integration pattern of soybean event pDAB4472-1606. These experiments generated data which demonstrated the integration and integrity of the aad-12 transgene within the soybean genome. Soybean event pDAB4472-1606 was characterized as a full length, simple integration event containing a single copy of the aad-12 PTU from plasmid pDAB4472.

Southern blot data suggested that a 7,188 bp T-strand fragment inserted into the genome of soybean event pDAB4472-1606. Detailed Southern blot analysis was conducted using a probe specific to the aad-12 gene and descriptive restriction enzymes which cleaved at sites located within the plasmid. This produces hybridizing fragments internal to the plasmid or fragments that spanned the junction of the plasmid with soybean genomic DNA (border fragments). The molecular sizes indicated from the Southern hybridization for the combination of the restriction enzymes and the probe were unique for the event, and thus established its identification patterns. These analyses also showed that the plasmid fragment had been inserted into soybean genomic DNA without rearrangements of the aad-12 PTU.

Example 2.1

Soybean Leaf Sample Collection and Genomic DNA (gDNA) Isolation

Genomic DNA was extracted from leaf tissue harvested from individual soybean plants containing soybean event pDAB4472-1606. In addition, gDNA was also isolated from a conventional soybean plant, Maverick, which contains the genetic background that is representative of the substance line, absent the aad-12 gene, to serve as a negative control.

Individual genomic DNA was extracted from leaf tissue following the modified CTAB method. Briefly, fresh or frozen leaf samples were individually ground in liquid nitrogen followed by the addition of approximately 25 mL extraction buffer and RNase-A (approximately 50 L) (Qiagen, Germantown, Md.) and Proteinase K (approximately 50 L) (Qiagen, Germantown, Md.). After about 1-2 hours of incubation at ~65° C. with gentle shaking, samples were spun down and the supernatants were extracted twice with equal volume of chloroform/octonal (24:1) (Sigma, St. Louis, Mo.). DNA was precipitated by mixing the supernatants with equal volume of precipitation buffer (1% CTAB, 50 mM Tris-HCl, and 10 mM EDTA). The precipitated DNA was dissolved in high salt TE buffer (1×TE pH8.0) followed by precipitation with isopropyl alcohol. The precipitated DNA was rinsed with 70% ethanol, air-dried, then dissolved in appropriate volume of 1×TE buffer (pH8.0). To check the quality of the resultant genomic DNA, an aliquot of the DNA samples were electrophoretically separated on a 1% agarose gel containing ethidium bromide (~1 μg/mL) with 1×TBE buffer. The gel was visualized under ultraviolet (UV) light to confirm that the DNA was not degraded and that the RNA had been removed by the RNase-A. The concentration of DNA in solution was determined using the Pico Green kit (Invitrogen, Carlsbad, Calif.) in a fluorometer (Bio-TEK, Winooski, Vt.).

Example 2.2

DNA Digestion and Separation

For molecular characterization of the soybean event pDAB4472-1606, nine micrograms (9 μg) of genomic DNA from soybean event pDAB4472-1606 and the control Maverick were digested by adding approximately eleven units of selected restriction enzyme per μg of DNA and the corresponding reaction buffer to each DNA sample. Each sample was incubated at approximately 37° C. overnight. The restriction enzymes HinD III, Nco I, Sph I, and Pst I were used for the digestions (New England Biolabs, Ipswich, Mass.). The positive hybridization control sample was prepared by combining plasmid DNA pDAB4472 with genomic DNA from the conventional control at a ratio of approximately equivalent to one copy of transgene per soybean genome, and digested using the same procedures and restriction enzyme as the test samples. DNA from the conventional soybean control, Maverick, was digested using the same procedures and restriction enzymes as the test samples to serve as a negative control.

The digested DNA samples were precipitated with Quick-Precip (Edge BioSystems) and resuspended in 1× Blue Juice (Invitrogen, Carlsbad, Calif.) to achieve the desired volume for gel loading. The DNA samples and molecular size markers were then electrophoresed through 0.8% agarose gels with 1×TBE buffer at 55-65 volts for approximately 18-22 hours to achieve fragment separation. The gels were stained with ethidium bromide and the DNA was visualized under ultraviolet (UV) light.

Example 2.3

Southern Transfer and Membrane Treatment

Southern blot analysis was performed essentially as described by Memelink et al., *Plant Mol. Biol. Manual*, F1:1-23 (1994). Briefly, following electrophoretic separation and visualization of the DNA fragments, the gels were depurinated with 0.25N HCl for approximately 20 minutes, and then exposed to a denaturing solution (AccuGENE, Rockland, Me.) for approximately 30 minutes followed by immersion in a neutralizing solution (AccuGENE, Rockland, Me.) for at least 30 minutes. Southern transfer was performed overnight onto nylon membranes (Roche Diagnostics, Indianapolis, Ind.) using a wicking system with 10×SSC. After transfer the membranes were washed with a 2×SSC solution and the DNA was bound to the membrane by UV crosslinking. This process produced Southern blot membranes ready for hybridization.

Example 2.4

DNA Probe Labeling, Hybridization, and Detection

The DNA fragments bound to the nylon membrane were detected using a labeled probe. Probes were generated by a PCR-based incorporation of a digoxigenin (DIG) labeled nucleotide, [DIG-11]-dUTP, into the DNA fragment amplified from plasmid pDAB4472 using primers specific to gene elements. Generation of DNA probes by PCR synthesis was carried out using a PCR DIG Probe Synthesis Kit (Roche Diagnostics, Indianapolis, Ind.) following the manufacturer's recommended procedures.

Labeled probes were analyzed by agarose gel electrophoresis to determine their quality and quantity. A desired amount of labeled probe was then used for hybridization to the target DNA on the nylon membranes for detection of the specific fragments using the procedures essentially as described for DIG Easy Hyb Solution (Roche Diagnostics, Indianapolis, Ind.). Briefly, nylon membrane blots containing fixed DNA were briefly washed with 2×SSC and pre-hybridized with 20-25 mL of pre-warmed DIG Easy Hyb solution in hybridization bottles at approximately 55-60° C. for a minimum of 30 minutes in a hybridization oven. The pre-hybridization solution was then decanted and replaced with ~20 mL of pre-warmed DIG Easy Hyb solution containing a desired amount of specific probes denatured by boiling in a water bath for approximately five minutes. The hybridization step was then conducted at approximately 55-61° C. overnight in the hybridization oven.

At the end of the probe hybridization, DIG Easy Hyb solutions containing the probes were decanted into clean tubes and stored at approximately −20° C. These probes could be reused for 3-5 times according to the manufacturer's recommended procedure. The membrane blots were rinsed briefly and washed twice in clean plastic containers with low stringency wash buffer (2×SSC, 0.1% SDS) for approximately five minutes at room temperature, followed by washing twice with high stringency wash buffer (0.1×SSC, 0.1% SDS) for 15 minutes each at approximately 65° C. The membrane blots were then transferred to other clean plastic containers and briefly washed with 1× washing buffer from the DIG Wash and Block Buffer Set (Roche Diagnostics, Indianapolis, Ind.) for approximately 2 minutes. This was followed by blocking in a 1× blocking buffer for a minimum of 30 minutes and incubation with anti-DIG-AP (alkaline phosphatase) antibody (Roche Diagnostics, Indianapolis, Ind.) in 1× blocking buffer also for a minimum of 30 minutes. After 2-3 washes with 1× washing buffer, specific DNA probes remain bound to the membrane blots and DIG-labeled DNA standards were visualized using CDP-Star Chemiluminescent Nucleic Acid Detection System (Roche Diagnostics, Indianapolis, Ind.) following the manufacturer's recommendation. Blots were exposed to chemiluminescent film (Roche Diagnostics, Indianapolis, Ind.) for one or more time points to detect hybridizing fragments and to visualize molecular size standards. Films were developed with an All-Pro 100 Plus film developer (Konica Minolta, Osaka, Japan) and images were scanned. The number and sizes of detected bands were documented for each probe. DIG-labeled DNA Molecular Weight Marker II (DIG MWM II), visible after DIG detection as described, was used to determine hybridizing fragment size on the Southern blots.

TABLE 1

Location and Length of Probes used in Southern Analysis.

| Probe Name | Genetic Element | Length (bp) |
| --- | --- | --- |
| aad-12 | aad-12 | 882 |
| SpecR | Spectinomycin resistance gene | 795 |
| OriRep | Ori Rep | 1087 |

Example 2.5

Southern Blot Results

Expected and observed fragment sizes with a particular digest and probe, based on the known restriction enzyme sites of the aad-12 PTU, are given in Table 2. Two types of fragments were identified from these digests and hybridizations: internal fragments where known enzyme sites flank the probe region and are completely contained within the insertion region of the aad-12 PTU, and border fragments where a known enzyme site is located at one end of the probe region and a second site is expected in the soybean genome. Border fragment sizes vary by event because, in most cases, DNA fragment integration sites are unique for each event. The border fragments provide a means to locate a restriction enzyme site relative to the integrated DNA and to evaluate the number of DNA insertions. Southern blot analyses completed on five generations of soybean containing soybean event pDAB4472-1606 produced data which suggested that a single, intact copy of aad-12 PTU from plasmid pDAB4472 was inserted into the soybean genome of soybean event pDAB4472-1606.

TABLE 2

Predicted and Observed Hybridizing Fragments in Southern Blot Analysis.

| DNA Probe | Restriction Enzymes | Samples | Expected Fragment Sizes (bp)[1] | Observed Fragment Size (bp)[2] | Figure |
|---|---|---|---|---|---|
| aad-12 | Hind III | pDAB4472 | 6082 | ~6100 | 2 |
| | | Maverick | none | none | |
| | | Soybean Event pDAB4472-1606 | >5783 | ~8100 | |
| | Sph I | pDAB4472 | 12548 | ~12500 | 3 |
| | | Maverick | none | none | |
| | | Soybean Event pDAB4472-1606 | >6639 | ~6700 | |
| | Hind III/Pst I | pDAB4472 | 3290 | ~3300 | 4 |
| | | Maverick | none | none | |
| | | Soybean Event pDAB4472-1606 | 3290 | ~3300 | |
| specR | Nco I | pDAB4472 | 4581 | ~4600 | 5 |
| | | Maverick | none | none | |
| | | Soybean Event pDAB4472-1606 | none | none | |
| OriRep | Nco I | pDAB4472 | 7439 | ~7400 | 5 |
| | | Maverick | none | none | |
| | | Soybean Event pDAB4472-1606 | none | none | |

[1]Expected fragment sizes are based on the plasmid map of pDAB4472.
[2]Observed fragment sizes are considered approximately from these analyses and are based on the indicated sizes of the DIG-labeled DNA Molecular Weight Marker II fragments.

Figure 2:
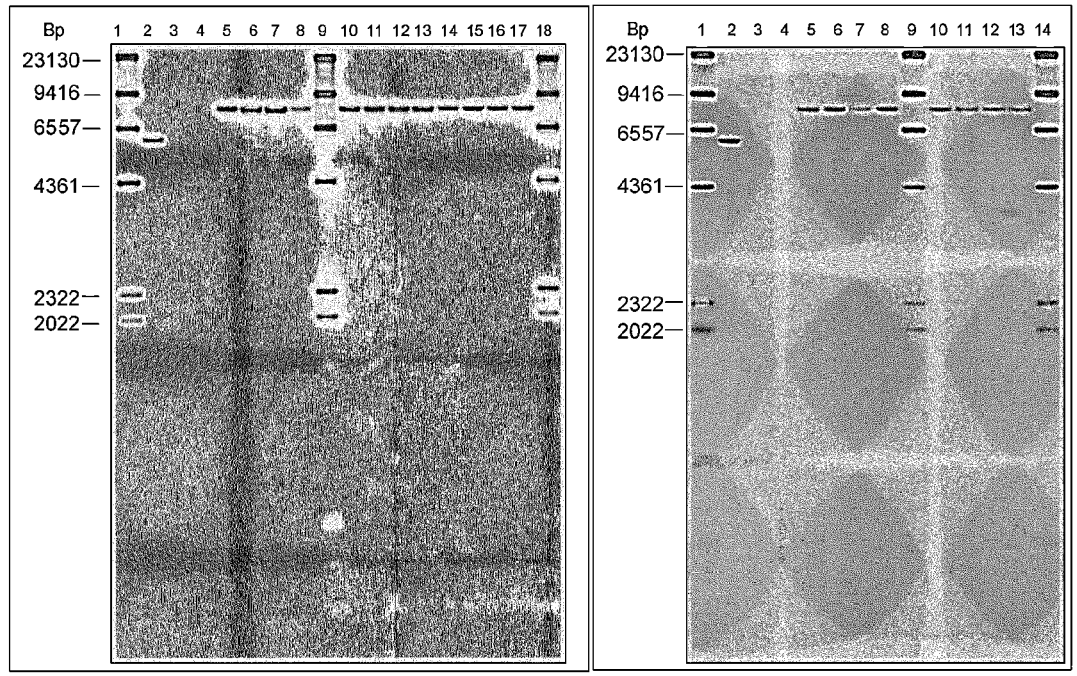
FIG. 2. Southern blot analysis of soybean event pDAB4472-1606 T2-T6 genomic DNA digested with Hind III and hybridized with aad-12 gene probe. (DIG MWM II: DIG-labeled DNA molecular weight marker; Maverick+ pDAB4472: positive control; maverick: negative control; 1606: soybean event pDAB4472-1606).
Figure 3:
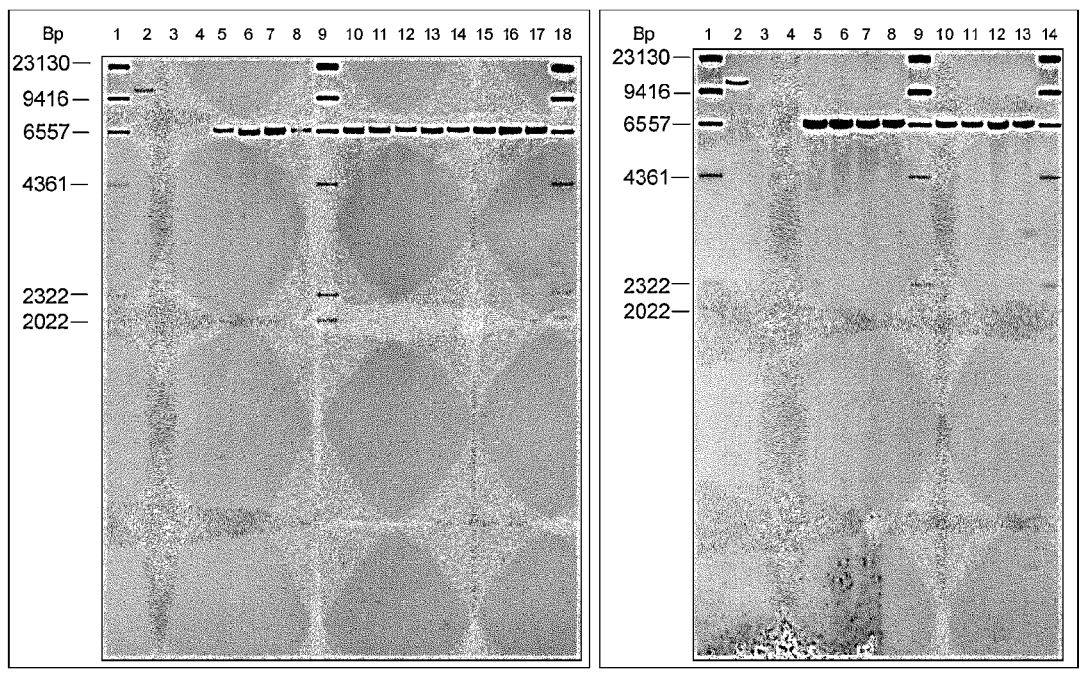
FIG. 3. Southern blot analysis of soybean event pDAB4472-1606 T2-T6 genomic DNA digested with Sph I and hybridized with aad-12 gene probe. (DIG MWM II: DIG-labeled DNA molecular weight marker; Maverick+ pDAB4472: positive control; maverick: negative control; 1606: soybean event pDAB4472-1606).
Figure 4:
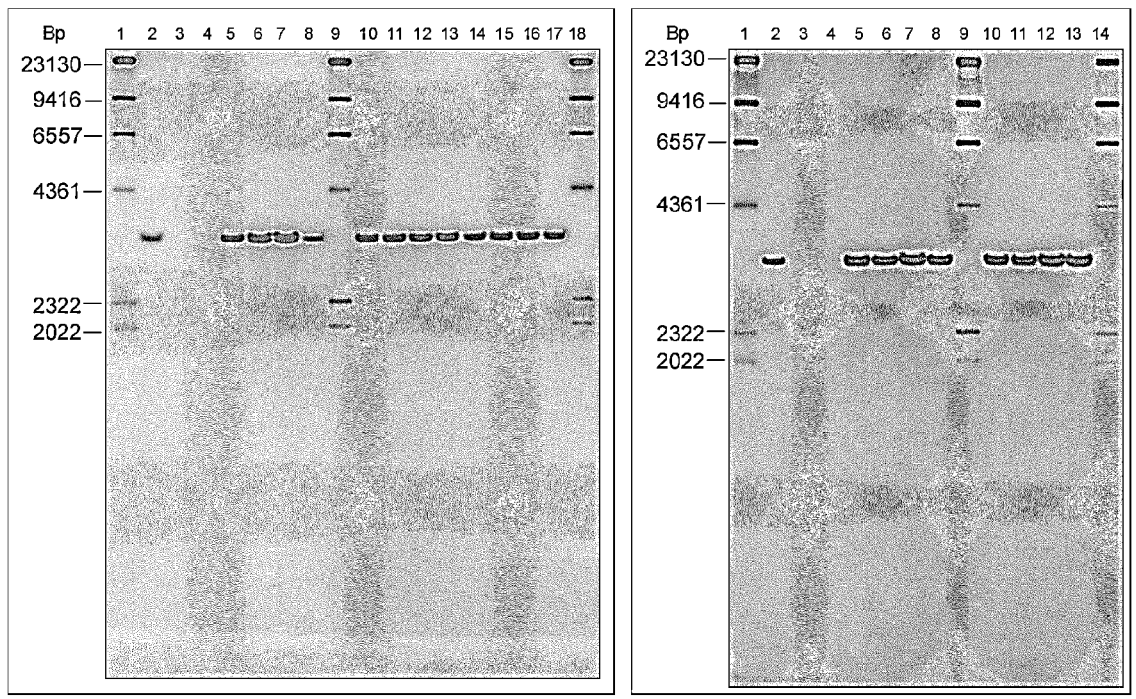
FIG. 4. Southern blot analysis of soybean event pDAB4472-1606 T2-T6 genomic DNA digested with Hind III/Pst I and hybridized with aad-12 gene probe. (DIG MWM II: DIG-labeled DNA molecular weight marker; Maverick+ pDAB4472: positive control; maverick: negative control; 1606: soybean event pDAB4472-1606).

Restriction enzymes Hind III and Sph I contain unique restriction sites within plasmid pDAB4472. Thus these enzymes were selected to characterize the two border fragments of aad-12 gene insert in soybean event pDAB4472-1606. Border fragments of >5,783 bp and >6,639 bp were predicted to hybridize with the aad-12 gene probe following Hind III and Sph I digest, respectively (Table 2). As shown in FIGS. 2 and 3, single aad-12 hybridization bands of ~8,100 bp and ~6,700 bp were observed when Hind III and Sph I were used, respectively. In addition, a combination of restriction enzymes Hind III and Pst I was selected to release a fragment of 3,290 bp containing the aad-12 plant transcription unit (PTU; promoter/gene/terminator) (Table 2). As shown in FIG. 4, this predicted 3,300 bp fragment was observed with the aad-12 gene probe following Hind III/Pst I digestion. Results obtained with all three enzyme (including the Hind III/Pst I enzyme combination) digestion of five distinct generations of soybean event pDAB4472-1606 genomic DNA samples followed by aad-12 gene probe hybridization indicated that a single intact copy of aad-12 PTU from plasmid pDAB4472 was inserted into the soybean genome of soybean event pDAB4472-1606 and the insertion is stable across all generations tested.

Example 2.6

Absence of Backbone Sequences

Figure 5:
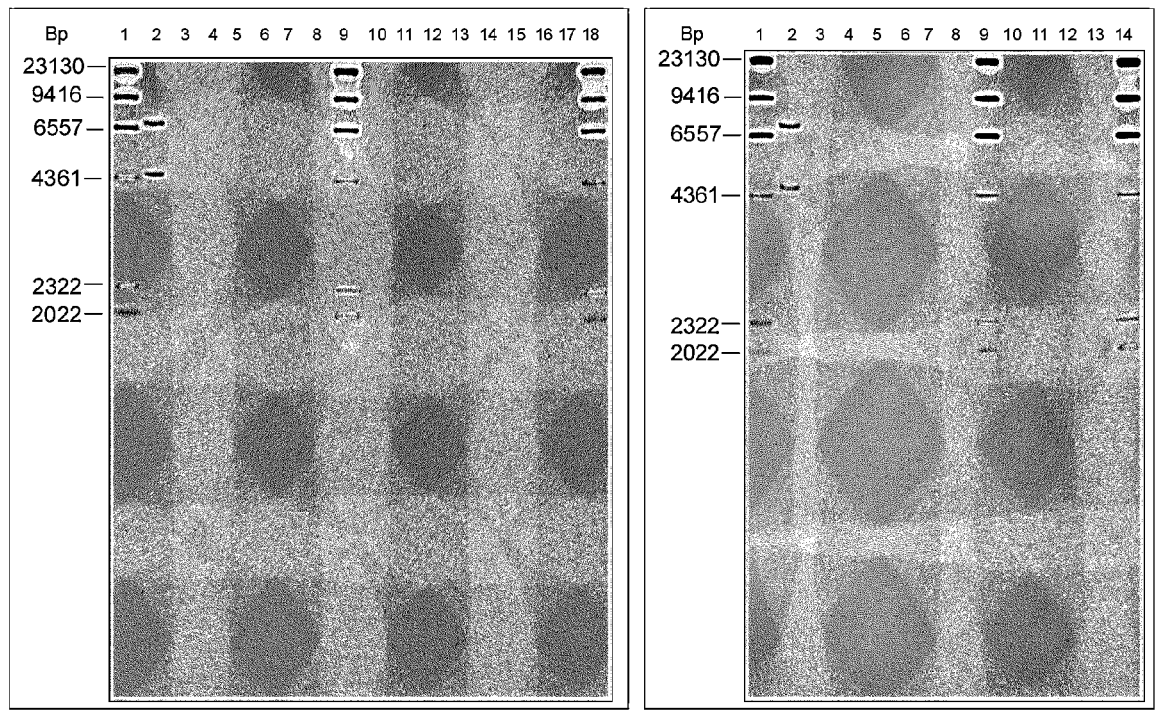
FIG. 5. Southern blot analysis of soybean event pDAB4472-1606 T2-T6 genomic DNA digested with Nco I and hybridized with OriRep and SpecR probes. (DIG MWM II: DIG-labeled DNA molecular weight marker; Maverick+ pDAB4472: positive control; Maverick: negative control; 1606: soybean event pDAB4472-1606).

Southern blot analysis was also conducted to verify the absence of the spectinomycin resistance gene and Ori Rep element in soybean event pDAB4472-1606. No specific hybridization to the spectinomycin resistance gene or the Ori Rep element is expected in soybean event pDAB4472-1606. In addition the appropriate positive (pDAB4472 plus Maverick) and negative (Maverick) controls were included for Southern analysis. As shown in FIG. 5, Following Nco I digestion and hybridized with mixture of specR gene and OriRep specific probes, two expected size bands of ~4,600 bp and ~7,400 bp were observed in the positive control sample (pDAB4472 plus maverick) but absent from samples of the negative control and soybean event pDAB4472-1606. This data indicates the absence of spectinomycin resistance gene and Ori Rep element in soybean event pDAB4472-1606.

Example 3

Cloning and Characterization of the Flanking Border Sequence of Soybean Event pDAS-1606

To characterize and describe the genomic insertion site, the sequence of the flanking genomic DNA border regions of soybean event pDAB4472-1606 were determined. In total, 3,224 bp of 5' flanking border sequence and 1,268 bp of 3' flanking border sequence were confirmed (SEQ ID NO:1). PCR amplification based on the soybean event pDAB4472-1606 border sequences validated that the border regions were of soybean origin and that the junction regions could be used for event-specific identification of soybean event pDAB4472-1606. Analysis of the sequence spanning the junction regions, including the flanking border sequences, did not identify any novel open reading frames (ORF>=150 codons) resulting from the T-strand insertion. In addition, the T-strand insertion site was characterized by cloning a genomic fragment corresponding to the region of the identified flanking border sequences from the genome of non-transgenic soybean. Comparison of soybean event pDAB4472-1606 with the wild type genomic sequence revealed a 1 bp deletion from the original locus and a 2 bp insertion at the 5' integration junction of the event.

Example 3.1

Genomic DNA Extraction and Quantification

Genomic DNA was extracted from lyophilized or freshly ground leaf tissues using a modified CTAB method. Following genomic DNA extraction, DNA samples were dissolved in 1×TE (10 mM Tris pH8.0, 1 mM EDTA) (Fluka, Sigma, St. Louis, Mo.) and quantified using the Pico Green method according to manufacturer's instructions (Molecular Probes, Eugene, Oreg.). For PCR analysis, DNA samples were diluted with molecular biology grade water (5 PRIME, Gaithersburg, Md.) resulting in a concentration of 10-100 ng/μL.

Example 3.2

PCR Primers

Figure 6:
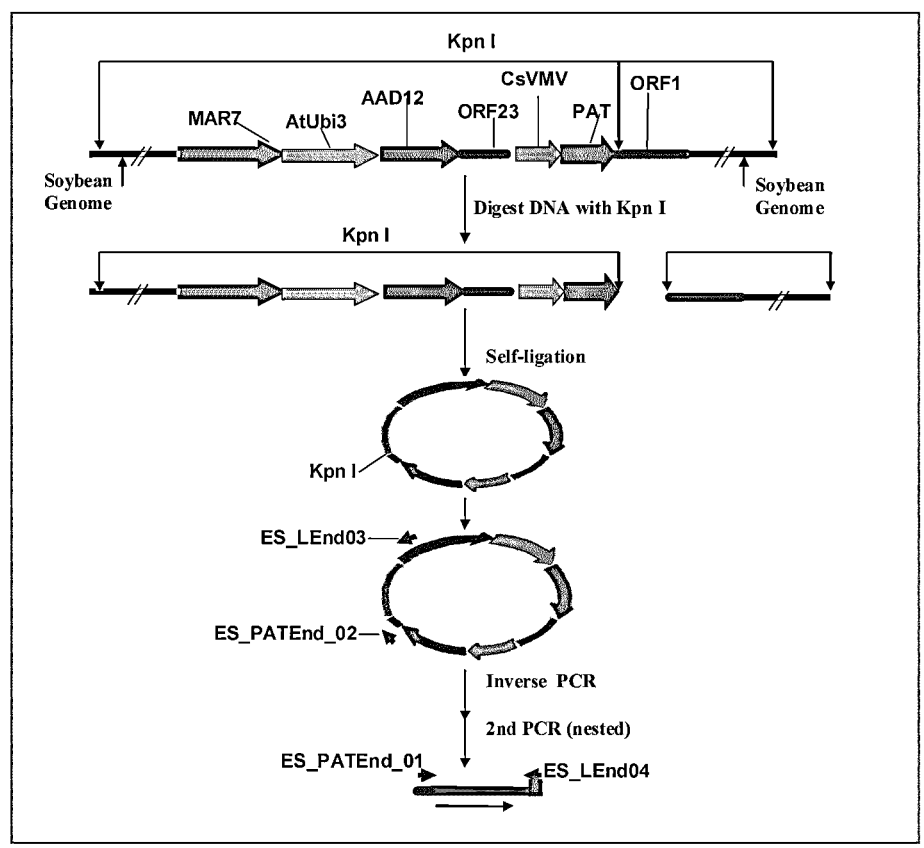
FIG. 6. Diagram of cloning the 5' Flanking Border Sequence from Soybean Event pDAB4472-1606 with Inverse PCR.

Table 3 lists the primer sequences that were used to clone and confirm the DNA insert and the flanking border regions of soybean event pDAB4472-1606, with positions and descriptions marked in FIG. 6. All primers were synthesized by Integrated DNA Technologies, Inc. (Coralville, Iowa). Primers were dissolved in water (5 PRIME, Gaithersburg, Md.) to a concentration of 100 μM for the stock solution and diluted with water to a concentration of 10 μM for the working solution.

TABLE 3

Conditions for genome walking soybean event pDAB4472-1606 to amplify the flanking border regions

| Target Sequence | Primer Set | Pre-denature (° C./min) | Denature (° C./sec.) | Anneal (° C./sec.) | Extension (° C./min: sec) | Denature (° C./sec.) | Anneal (° C./sec.) | Extension (° C./min: sec.) | Final Extension (° C./min) |
|---|---|---|---|---|---|---|---|---|---|
| 5' border | ES_Lend03 (SEQ ID NO: 2) ES_PATEnd02 (SEQ ID NO: 3) | 95/3 | — | — | — | 95/30 30 cycles | — | 68/15:00 | 72/10 |
| 5' border (nested) | ES_Lend04 (SEQ ID NO: 4) ES_PATEnd01 (SEQ ID NO: 5) | 95/3 | — | — | — | 95/30 30 cycles | — | 68/15:00 | 72/10 |
| 5' border | ES_LEnd_03 AP1 | 95/3 | 95/30 | 68→64 (−0.5/cycle)/30 8 cycles | 68/10:00 | 95/30 | 64/30 22 cycles | 68/10:00 | 72/10 |
| 5' border (nested) | ES_LEnd_04/ AP2 | 95/3 | 95/30 | 68→64 (−0.5/cycle)/30 8 cycles | 68/10:00 | 95/30 | 64/30 24 cycles | 68/10:00 | 72/10 |
| 3' border | ES_PATEnd_03 (SEQ ID NO: 6)/AP1 | 95/3 | 95/30 | 68→64 (−0.5/cycle)/30 8 cycles | 68/10:00 | 95/30 | 64/30 22 cycles | 68/10:00 | 72/10 |
| 3' border (nested) | ES_PATEnd_04 (SEQ ID NO: 7)/AP2 | 95/3 | 95/30 | 68→64 (−0.5/cycle)/30 8 cycles | 68/10:00 | 95/30 | 64/30 24 cycles | 68/10:00 | 72/10 |

TABLE 4

Conditions for standard PCR amplification of the border regions and event-specific sequences in soybean event pDAB4472-1606

| Target Sequence | Primer Set | PCR Mixture | Pre-denature (° C./min) | Denature (° C./sec.) | Anneal (° C./sec.) | Extension (° C./min: sec.) | Final Extension (° C./min) |
|---|---|---|---|---|---|---|---|
| 5' border | 56LEndG01 (SEQ ID NO: 8) AIILEnd05 (SEQ ID NO: 16) | B | 95/3 | 95/30 | 60/30 35 cycles | 68/5:00 | 72/10 |
| 5' border | 56LEndG02 (SEQ ID NO: 9) AIILEnd05 | B | 95/3 | 95/30 | 60/30 35 cycles | 68/5:00 | 72/10 |
| specific sequence in 5' end insert junction | Soy1606-F (SEQ ID NO: 19) Soy1606-R (SEQ ID NO: 20) | C | 95/15 | 94/30 | 60/30 35 cycles | 72/1:00 | 72/10 |
| 3' border | 56PATG01 (SEQ ID NO: 12) PATEnd05 (SEQ ID NO: 17) | B | 95/3 | 95/30 | 60/30 35 cycles | 68/5:00 | 72/10 |

TABLE 4-continued

Conditions for standard PCR amplification of the border regions
and event-specific sequences in soybean event pDAB4472-1606

| Target Sequence | Primer Set | PCR Mixture | Pre-denature (° C./min) | Denature (° C./sec.) | Anneal (° C./sec.) | Extension (° C./min: sec.) | Final Extension (° C./min) |
|---|---|---|---|---|---|---|---|
| 3' border | 56PATG02 (SEQ ID NO: 13) PATEnd06 (SEQ ID NO: 18) | B | 95/3 | 95/30 | 60/30 35 cycles | 68/5:00 | 72/10 |
| Across the insert locus | 56LEndG03 (SEQ ID NO: 10) 56PATG03 (SEQ ID NO: 14) | A | 95/3 | 95/30 | 60/30 35 cycles | 68/5:00 | 72/10 |
| Across the insert locus | 56LEndG04 (SEQ ID NO: 11) 56PATG05 (SEQ ID NO: 15) | A | 95/3 | 95/30 | 60/30 35 cycles | 68/5:00 | 72/10 |

TABLE 5

PCR mixture for standard PCR amplification of the border regions
and event specific sequences in soybean event pDAB4472-1606.

| PCR Mixture A | | PCR Mixture B | |
|---|---|---|---|
| Reagent | 1 x reaction (µL) | Reagent | 1 x reaction (µL) |
| H20 | 29 | H20 | 30.5 |
| 10X PCR buffer II (Mg-plus) | 5 | 10X PCR buffer II (Mg-plus) | 5 |
| MgCl$_2$[25 mM] | 1.5 | MgCl$_2$[25 mM] | 0 |
| dNTP[2.5 mM] | 8 | dNTP[2.5 mM] | 8 |
| primer1 (10 µM) | 1 | primer1 (10 µM) | 1 |
| primer2 (10 µM) | 1 | primer2 (10 µM) | 1 |
| DNA[10 ng/uL] | 4 | DNA[10 ng/uL] | 4 |
| LA Taq (5 U/ul) | 0.5 | LA Taq (5 U/ul) | 0.5 |
| rxn vol: | 50 | rxn vol: | 50 |

| PCR Mixture C | | | PCR Mixture D | |
|---|---|---|---|---|
| PCR Mix | Reagent | Reagent | Reagent | 1 x reaction (µL) |
| H2O | H20 | H20 | H20 | 32 |
| 10xQIA buffer | 10X PCR buffer II (Mg-plus) | 10X PCR buffer II (Mg-plus) | | 5 |
| MgCl$_2$ | MgCl$_2$[25 mM] | MgCl$_2$[25 mM] | | 1.5 |
| dNTP[2.5 mM] | dNTP[2.5 mM] | dNTP[2.5 mM] | | 8 |
| primer1 (10 µM) | primer1 (10 µM) | primer1 (10 µM) | | 1 |
| primer2 (10 µM) | primer2 (10 µM) | primer2 (10 µM) | | 1 |
| DNA[10 ng/uL] | DNA Template | DNA Template | | 1 |
| QIA Hstaq(5 U/ul) | LA Taq (5 U/ul) | LA Taq (5 U/ul) | | 0.5 |
| rxn vol: | rxn vol: | rxn vol: | | 50 |

Example 3.3

Inverse PCR

Inverse PCR was used to clone and sequence the 5' flanking border sequences of aad-12 soybean event pDAB4472-1606. Two micrograms (2 µg) of genomic DNA from AAD12 soybean event pDAB4472-1606 was digested with Kpn I, following by self-ligation of the DNA fragment with T4 ligase. The ligation product was used as a PCR template for primary PCR amplification with the construct specific primer pair of ES_PATEnd02 and ES_Lend03. One microliter (1 µl) from the 1st round PCR reaction was used as template for a 2nd round of PCR amplification using the nested construct-specific primer pair of ES_PATEnd01 and ES_Lend04 (Table 3, 4 and FIG. 6). Further analysis of the PCR amplified products is described below.

Example 3.4

Genome Walking

Figure 7:
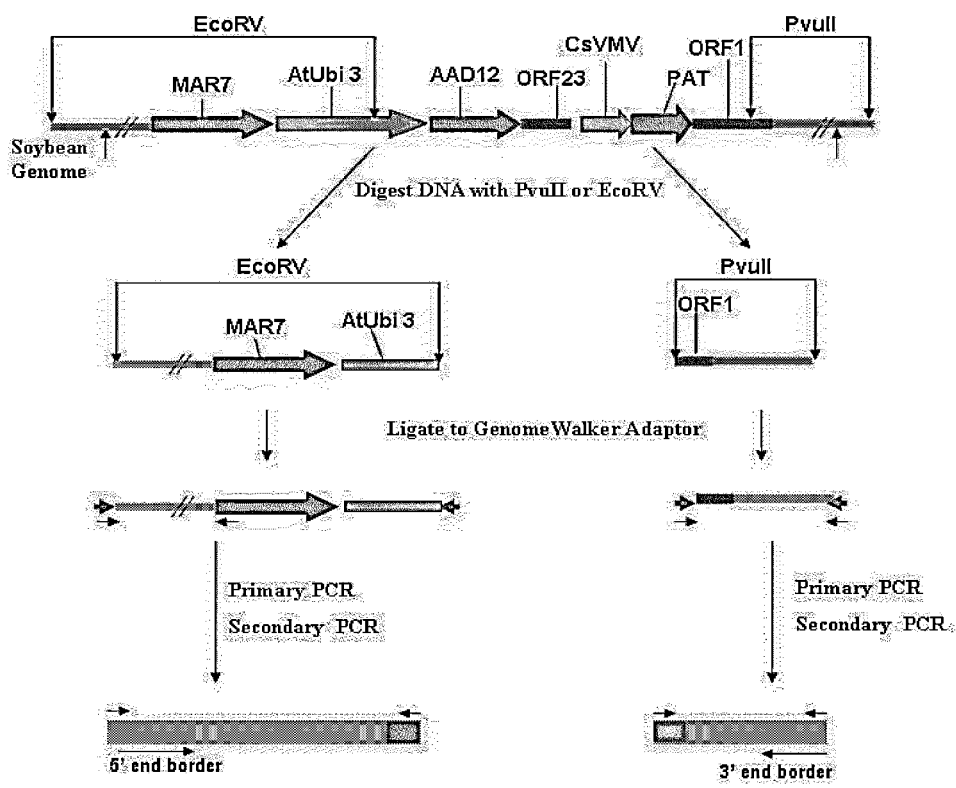
FIG. 7. Genomic DNA of the soybean event pDAB4472-1606 was digested with EcoRV, or Pvu II and used to generate corresponding GENOMEWALKER™ libraries, which were used as templates to amplify the target DNA sequences.

The GenomeWalker™ Universal Kit (Clontech Laboratories, Inc., Mountain View, Calif.) was used to clone the 5' and 3' flanking border regions of the pDAB4472 T-strand insert for soybean event pDAB4472-1606 following manufacturer's instructions. Approximately 2 µg of genomic DNA from soybean event pDAB4472-1606 was digested overnight with EcoRV and PvuII (FIG. 7). DNA digests were purified using the DNA Clean & Concentrator™-25 (ZYMO Research, Orange, Calif.) followed by ligation to GenomeWalker™ adaptors to construct GenomeWalker™ libraries. Each GenomeWalker™ library was used as a DNA template for primary PCR amplification with adaptor primer AP1 (provided in the kit) and a construct-specific primer ES_LEnd03 or ES_PATEnd03 (Table 3). One microliter (1 µL) of 1:25 dilution of primary PCR reaction was then used as template for the secondary PCR amplification with the nested adaptor primer AP2 provided in the kit and a nested construct-specific primer ES_LEnd04 or ES_PATEnd04 (Tables 3, 5, and FIG. 7).

Example 3.5

Conventional PCR

Standard PCR was used to clone and confirm the insert and border sequence of soybean event pDAB4472-1606. TaKaRa LA Taq™ (Takara Bio Inc, Shiga, Japan), HotStarTaq™

DNA Polymerase (Qiagen, Valencia, Calif.), High Fidelity™ PCR Kit (Roche Diagnostics, Inc), or the Easy-A™ High Fidelity Polymerase Kit (Stratagene, LaJolla, Calif.) were used for conventional PCR amplification according to the manufacturer's recommended procedures. Specific PCR conditions and amplicon descriptions are listed in Tables 3, 4, and 5.

Example 3.6

PCR Product Detection, Purification, Sub-Cloning of PCR Products, and Sequencing PCR products were inspected by electrophoresis using a 1.2% or 2% E-Gel® (Invitrogen, Carlsbad, Calif.) according to product instruction. Fragment size was estimated by comparison with the DNA markers. If necessary, PCR fragments were purified by excising the fragments from a 1% agarose gel in 1×TBE (89 mM Tris-Borate, 2 mM EDTA, pH 8.3) stained with ethidium bromide using the QIAquick Gel Extraction Kit (Qiagen, Valencia, Calif.).

PCR fragments were sub-cloned into the pCR4-TOPO® vector using the TOPO TA Cloning® Kit for Sequencing (Invitrogen, Carlsbad, Calif.) according to the product instructions. Specifically, two to five microliters of the TOPO® cloning reaction was transformed into the One Shot chemically competent TOP10 cells following manufacturer's instruction. Cloned fragments were verified by minipreparation of the plasmid DNA (QIAprep Spin Miniprep Kit, Qiagen, CA) followed by restriction digestion with EcoRI or by direct colony PCR using T3 and T7 primers. Plasmid DNA or glycerol stock of selected colonies was then outsourced for sequencing.

After sub-cloning the putative PCR products were sequenced to confirm that the expected DNA fragments had been cloned. The colonies containing the expected DNA fragments were selected to complete double-strand full length sequencing by primer walking. All sequencing was outsourced to Cogenics (Houston, Tex.).

Final assembly of insert and border sequences was completed using Sequencher® software (Gene Codes Corporation, Ann Arbor, Mich.). Annotation of the insert and its flanking border sequences of soybean event pDAB4472-1606 were performed using Vector NTI (Invitrogen, Carlsbad, Calif.).

Homology searching was performed using the BLAST program against the GenBank non-redundant nucleotide database. Open reading frame (ORF) analysis using Vector NTI (Invitrogen, Carlsbad, Calif.) was performed to identify ORFs (>=150 codons) in the full insert and flanking border sequences of soybean event pDAB4472-1606, and the original locus of the wildtype Maverick soybean line.

Example 3.7

5' End Border Sequence

Two approaches were used to clone the 5' flanking border sequence of AAD12 soybean event pDAB4472-1606; inverse PCR and genome walking. A DNA fragment with size of about 3.5 kb, as expected based on the previous Southern data, was amplified by inverse PCR with specific nested primer sets (FIG. 6). The PCR fragment was cloned into a pCR®2.1-TOPO® vector. Five colonies were randomly picked for end sequencing at both strands. The clones, which contain both PCR primers, were completely sequenced. The sequencing result revealed that one end of the 3.5 kb DNA fragment matched with the 5' end junction of T-DNA Border B from the transgene and the other end matched the sequences between primer ES_PATEnd01 and the Kpn I site in the plasmid used for transformation (FIG. 6).

A DNA fragment was amplified from soybean event pDAB4472-1606_GenomeWalker™ library using the specific nested primer set for the 5' end of the transgene. A ~2.4 kb fragment from the EcoRV GenomeWalker™ library was observed. The fragment was cloned into pCR4-TOPO® vector. Five colonies were randomly picked for end sequencing to generate nucleotide sequence data. The colonies containing the sequences of both specific nested PCR primers were selected to obtain the full sequences by primer walking. Sequence analysis revealed that the clone amplified from soybean event pDAB4472-1606 EcoRV GenomeWalker™ library contained a 2,440 bp DNA fragment, which overlapped with the DNA fragment obtained from inverse PCR clone at region between primer ES_LEnd04 and the EcoRV site. These DNA fragments all contained the 5' end junction of T-strand border B in the transgene, indicating that they were amplified from the same region of the 5' end transgene insert and its flanking border in soybean event pDAB4472-1606. The resultant 3,224 bp soybean genomic sequence was perfectly aligned to *Glycine max* cultivar Williams 82 clone BAC 56G2 (GenBank: EF623856.1) and BAC 27P17 (GenBank: EF623855.1) in GenBank.

Example 3.8

3' End Border Sequence

A DNA fragment with size of about 1.5 kb was amplified from soybean event pDAB4472-1606 Pvu II GenomeWalker™ library using the specific nested primer set for the 3' end of the transgene. The DNA fragment was then cloned into a pCR®4-TOPO® vector. Five colonies were randomly picked for end sequencing. All five clones contained the sequences of both Primer AP2 and Primer ES_PATEnd04. Complete sequencing of these clones resulted in a 1,555 bp consensus DNA fragment. Sequence analysis disclosed that the 1,555 bp fragment comprised of a 284 bp fragment from the 3' end region of T-strand Border A and a 1,268 bp fragment from soybean genomic DNA. BLAST search revealed this 1,268 bp soybean DNA sequence has 100% identity with *Glycine max* cultivar Williams 82 clone BAC 56G2 and BAC 27P17 (GenBank: EF623856.1) and BAC 27P17 (GenBank: EF623855.1).

Example 3.9

Confirmation of Soybean Genomic Sequences

Figure 8:
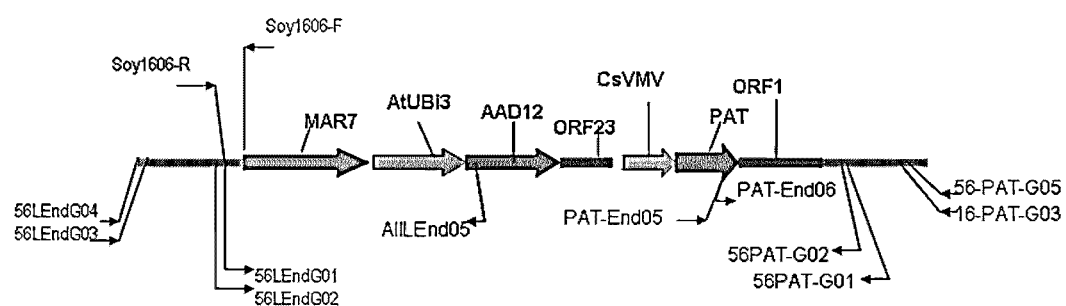
FIG. 8. The schematic diagram depicts the primer locations for confirming the full length sequence of the soybean event pDAB4472-1606 from 5' to 3' borders.

To confirm the insertion site of soybean event pDAB4472-1606 transgene in the soybean genome, PCR was carried out with different pairs of primers (FIG. 8 and Table 4). Genomic DNA from soybean event pDAB4472-1606 and other transgenic or non-transgenic soybean lines was used as templates. Thus, to confirm if the obtained 5' end border sequences are correct, an aad-12 specific primer, for example AIILEnd05, and two primers designed according to the 5' end border sequence, designated 56LEndG01 and 56LEndG02, were used for amplifying the DNA segment that spans the aad-12 gene to 5' end border sequence. Similarly, for confirmation of the cloned 3' end border sequence, two pat specific primers, for example PAT-End05 and PAT-End06, and two primers designed according to the 3' end border sequence, designated 56PATG01 and 56PATG02, were used for amplifying DNA segments that span the pat gene to 3' end border sequence. DNA fragments with predicted sizes were amplified only from the genomic DNA of soybean event pDAB4472-1606 with each primer pair, one primer located on the flanking border of soybean event pDAB4472-1606 and one transgene specific primer, but not from DNA samples from other transgenic soybean lines or non-transgenic control. The results indicate that the cloned 5' and 3' border sequences are the flanking border sequences of the T-strand insert in soybean event pDAB4472-1606.

To further confirm the T-strand insertion in the soybean genome, a PCR amplification spanning the two soybean sequences was completed. Two primers designed according to the 5' end border sequence, 56LEndG03 and 56LEndG04, and two primers for the 3' end border sequence, 56PATG03 and 56PATG05, were used to amplify DNA segments that contain the entire transgene, the 5' end border sequence, and the 3' border sequence. As expected, PCR amplification with the primer pair of 56LEndG03 and 56PATG03 amplified an approximately 10 kb DNA fragment from the genomic DNA of soybean event pDAB4472-1606 and a 2.7 kb DNA fragment from the non-transgenic soybean controls and other soybean transgenic lines. Similarly, PCR reactions completed with the primer pair of 56LEndG04 and 56PATG05 produced an approximately 10 kb DNA fragment from the sample of soybean event pDAB4472-1606 and a 2.9 kb DNA fragment from all the other soybean control lines, correspondingly. It was noted that a faint band with size of about 5 kb was visible in all the soybean samples except soybean event pDAB4472-1606 when the primer pair of 56LEndG03 and 56PAT03 were used for PCR, suggesting that this faint band resulted from nonspecific amplification in soybean genome with this pair of primers. Similarly, a faint band with size of about 5.5 kb was visible in all the soybean samples except soybean event pDAB4472-1606 when the primer pair of 56LEndG04 and 56PAT05 was used for PCR. Moreover, when the primer pair of 56LEndG04 and 56PAT05 was used for PCR, non specific amplification with size of about 700 bp was evident in all the soybean samples.

Example 3.10

Confirmation of Soybean Genomic Sequences

The 2.7 kb and 2.9 kb amplified DNA fragments, using the primer pair of 56LEndG03 and 56PATG03 and the primer pair of 56LEndG04 and 56PATG05, respectively, from non-transgenic soybean line Maverick were cloned and sequenced. These sequences were matched with each other and aligned with the cloned 5' and 3' border sequences from soybean event pDAB4472-1606. The cloned DNA sequence contained the locus where the T-strand of pDAB4472 was integrated into soybean event pDAB4472-1606. Alignment analysis revealed a 1 bp deletion from the original locus and a 2 bp insertion at 5' integration junction. No open reading frames (>/=450 bp, 150 aa) were identified in the soybean genomic region of the original locus that was cloned.

Example 4

Characterization of AAD12 Protein in Soybean Event DAS-1606

The biochemical properties of the recombinant AAD12 protein derived from the soybean event pDAB4472-1606 were characterized. Quantitative enzyme-linked immunosorbent assay (ELISA), sodium dodecyl sulfate polyacrylamide gel electrophoresis (SDS-PAGE, stained with Coomassie blue and glycoprotein detection methods), western blot, immunodiagnostic test strip assays, matrix assisted laser desorption/ionization time-of-flight mass spectrometry (MALDI-TOF MS) and protein sequencing analysis by tandem MS are biochemical assays known within the art that can be used to characterize the biochemical properties of the protein and confirm expression of AAD12 protein.

Example 4.1

Expression of the AAD12 Protein in Plant Tissues

Levels of AAD12 protein were determined in soybean event pDAB4472-1606. The soluble, extractable AAD12 protein was measured using a quantitative enzyme-linked immunosorbent assay (ELISA) method from soybean leaf tissue.

Samples of soybean tissues were isolated from the test plants and prepared for expression analysis. The AAD12 protein was extracted from soybean plant tissues with a phosphate buffered saline solution containing the detergent Tween-20 (PBST) containing 0.5% Bovine Serum Albumin (BSA). The plant tissue was centrifuged; the aqueous supernatant was collected, diluted with appropriate buffer as necessary, and analyzed using an AAD12 ELISA kit in a sandwich format. The kit was used following the manufacturer's suggested protocol. This assay measured the native tetramer AAD12 protein.

Figure 9:
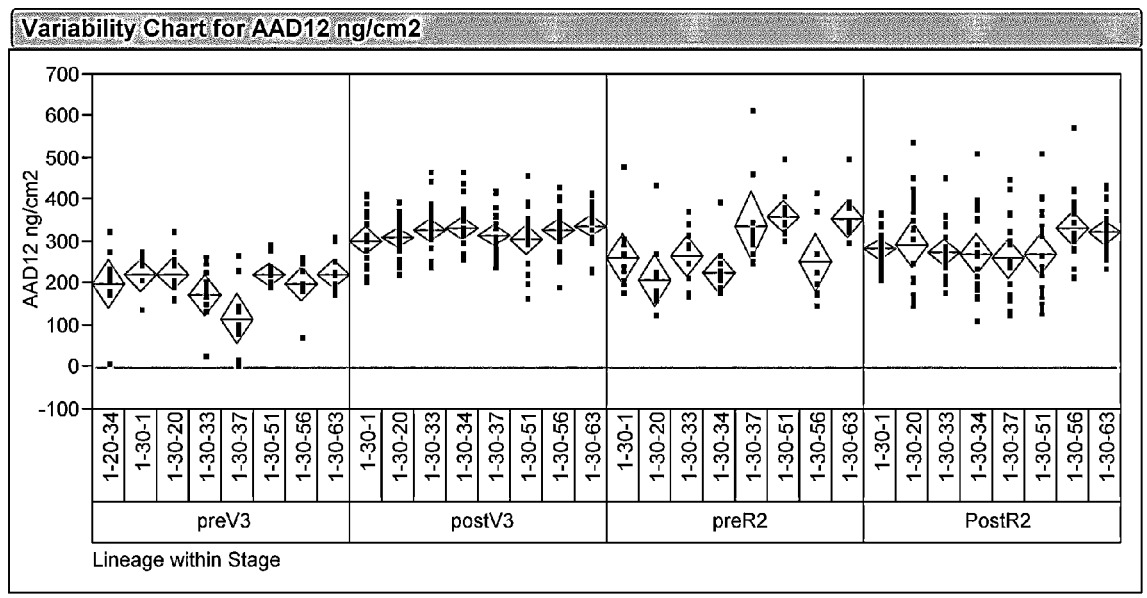
FIG. 9: Expression levels through the plant lifecycle.

Detection analysis was performed to investigate the expression stability and inheritability both vertically (between generations) and horizontally (between lineages) in soybean event pDAB4472-1606. At the T4 generation soybean event pDAB4472-1606 expression was stable (not segregating) and consistent across all lineages (FIG. 9).

Field expression level studies at various plant stages were performed on soybean event pDAB4472-1606 at pre V3, post V3, pre R2, and post R2. Expression values were similar for all the sprayed treatments as well as for the plots sprayed and unsprayed with 2,4-D herbicide. A 2× spray rate (2,240 gm ae/ha of 2,4-D) was applied and no significant injury was observed on the plants at any point of the study. Average expression across all lineages in pre V3 plant stage was 200 ug/cm$^2$. After spraying 2,4-D the expression remained stable averaging 300 ug/cm$^2$ across lineages. By the time the soybeans reached pre R2 the average expression had dropped slightly to an average of 250 ug/cm$^2$. After spraying 2,4-D the expression post R2 had remained at the previous average of 250 ug/cm$^2$. See FIG. 9.

Example 5

Event Specific Taqman Assay

An event specific Taqman assay was developed to detect the presence of soybean event pDAB4472-1606 and to determine zygosity status of plants in breeding populations. To develop an event specific assay, specific Taqman primers and probes were designed according to the DNA sequences located in the 5' insert-to-plant junction. For specific detection of soybean event pDAB4472-1606, a 133 bp DNA fragment that spans this 5' integration junction was amplified using two specific primers. The amplification of this PCR product was measured by a target-specific MGB probe synthesized by Applied Biosystems containing the FAM reporter at its 5' end. Specificity of this Taqman detection method for soybean event pDAB4472-1606 was tested against 15 different aad-12 soybean events and non-transgenic soybean variety (Maverick) in duplex format with the soybean specific endogenous reference gene, lectin.

Example 5.1 gDNA Isolation

Genomic DNA samples from 16 different soybean events and non-transgenic soybean varieties were tested in this study. Genomic DNA was extracted using the Qiagen DNeasy 96 Plant Kit. Fresh soybean leaf discs, 8 punches per sample, were used for gDNA extraction using a modified Qiagen DNeasy 96 Plant Kit protocol. The gDNA was quantified with the Pico Green method according to vendor's instructions (Molecular Probes, Eugene, Oreg.). Samples were diluted with DNase-free water resulting in a concentration of 10 ng/µL for the purpose of this study.

Example 5.2

Taqman Assay and Results

Specific Taqman primers and probes were designed for soybean event pDAB4472-1606 specific Taqman assay. These reagents can be used with the conditions listed below to detect soybean event pDAB4472-1606 within the soybean genome. Table 6 lists the primer and probe sequences that were developed specifically for the detection of event pDAB4472-1606.

TABLE 6

PCR Primers and Probes

| Name | Description | 5' to 3' sequence |
|---|---|---|
| Event Target Reaction | | |
| Soy1606-F (SEQ ID NO: 25) | Forward Primer | CGGTTAGGATCCGGTGAGTAATATT |
| Soy1606-R (SEQ ID NO: 26) | Reverse Primer | GCCATTAATTATAGCGGTGTTTGC |
| Soy1606-Probe (SEQ ID NO: 21) | Probe | FAM- CCTTGCAAAATTC -MGB |
| Lectin Reference System Reaction | | |
| ZN_007 (SEQ ID NO: 22) | Forward Primer | SEQ ID NO: 22 TCCCGAGTGGGTGAGGATAG |
| ZN_008 (SEQ ID NO: 23) | Reverse Primer | SEQ ID NO: 23 TCATGCGATTCCCCAGGTAT |
| ZN_LT_002 (SEQ ID NO: 24) | Probe | SEQ ID NO: 24 HEX- TTCTCTGCTGCCACGGGACTCGA-BHQ1 |

The multiplex PCR conditions for amplification are as follows: 1×PCR buffer, 0.5-2.5 mM $MgCl_2$, 0.2 mM dNTP, 0.2 µM Primer Soy1606-F, 0.2 µM Primer Soy1606-R, 0.2 µM Primer Z__007, 0.2 µM Primer ZN__008, 0.08 µM Soy1606-Probe, 0.08 uM Lectin probe ZN_LT__002, 40 U/mL HotStart Tag, 30 ng gDNA in a total reaction of 25 µl. The cocktail was amplified using the following conditions: i) 95° C. for 15 min, ii) 95° C. for 20 sec, iii) 60° C. for 60 sec, iv) repeat step ii-iii for 35 cycles, v) 4° C. hold. The Real time PCR was carried out on the Bio-rad iCycler™ and ABI Gene Amp PCR System 9700 thermocylers. Data analysis was based on measurement of the cycle threshold (CT), which is the PCR cycle number when the fluorescence measurement reaches a set value. CT value was calculated automatically by iCycler software.

The Taqman detection method for soybean event pDAB4472-1606 was tested against 16 different aad-12 soybean events and non-transgenic soybean varieties in duplex format with soybean specific endogenous lectin as a reference gene. This assay specifically detected the soybean event pDAB4472-1606 and did not produce or amplify any false-positive results from the controls (i.e. the different aad-12 soybean events and non-transgenic soybean varieties). The event specific primers and probes can be used for the detection of the soybean event pDAB4472-1606 and these conditions and reagents are applicable for zygosity assays.

Example 6

Methylation Detection of AAD-12 Soybean Event pDAB4472-1606 via Southern Blot

In transgenic plants, an introduced transgene can undergo silencing after integration into the plant genome. Subsequent expression of the transgene can be inhibited at the transcriptional level and/or the post-transcriptional level. Transcriptional gene silencing has been reported to be associated with methylation of the transgene, its promoter and other relevant sequences (Stam et al., *Annals of Botany* 79 3+/−12 (1997)). To detect methylation in specific sequences, methylation-sensitive restriction enzymes are used to digest DNA. These restriction enzymes are unable to cleave DNA which is methylated. Southern blot analysis is used to analyze the DNA fragments produce by the digestions. When specific sites are methylated, the enzymes cannot cleave the DNA. This results in the production of higher molecular weight DNA fragments which are detected on Southern blots. Southern-blot based methylation analysis was performed to determine the methylation status of the transgene of event pDAB4472-1606. The assay was conducted using probes specific to add-12 gene and its promoter. No methylation was detected by using two different restriction enzymes.

Example 6.1

Soybean Leaf Sample Collection and Genomic DNA (gDNA) Isolation gDNA prepared from leaf of the individual plants of the soybean event pDAB4472-1606 and non-transgenic soybean line Maverick. Genomic DNA was isolated from lyophilized leaf samples using the traditional CTAB method. Following extraction, the DNA was quantified using Pico Green reagent (Invitrogen, Carlsbad, Calif.).

Example 6.2

DNA Digestion and Separation

For molecular characterization of the DNA, nine micrograms of genomic DNA from soybean Event pDAB4472-1606 and non-transgenic soybean line Maverick were digested by adding approximately five units of selected restriction enzyme per µg of DNA and the corresponding reaction buffer to each DNA sample. Each sample was incubated at approximately 37° C. overnight. The restriction enzymes Aci I and Hyp188III were used for the digests (New England Biolabs, Ipswich, Mass.). DNA from the non-transgenic soybean Maverick was digested using the same procedures and restriction enzymes as the test samples to serve as a control. The digested DNA samples were precipitated with isopropanol after adding NaCl to a final concentration of 0.1 M and resuspended in 20 ul of 1× loading buffer (0.1% bromophenol blue, 100 mM EDTA, 50% glycerol, 10 mM Tris pH 7.5). The DNA samples and molecular size markers were then electrophoresed through 0.85% agarose gels with 0.4×TAE buffer (Fisher Scientific, Pittsburgh, Pa.) at 35 volts for approximately 18-22 hours to achieve fragment separation. The gels were stained with ethidium bromide (Invitrogen, Carlsbad, Calif.) and the DNA was visualized under ultraviolet (UV) light.

Example 6.3

Southern Transfer and Membrane Treatment

Southern blot analysis was performed as described by Severson (RFLP analysis of insect genomes, *The Mol. Bio. of Insect Disease Vectors: A Method Manual*, ed. Crampton et al., Chapman and Hall, London, pp. 309-320 (1997)). Following electrophoretic separation and visualization of the DNA fragments under UV light, the gels were exposed to a denaturing solution (150 m M NaOH, 3 mM EDTA) for approximately 20 minutes followed by neutralizing solution (150 mM NaPO4, pH 7.8) for at least 20 minutes. Southern transfer was performed overnight onto nylon membranes using a wicking system with transfer buffer (25 mM Sodium Pyrophosphate, pH 10). After transfer the membranes were baked at 65° C. for about 2 hours. This process resulted in Southern blot membranes ready for hybridization.

Example 6.4

DNA Probe Labeling and Hybridization

The DNA fragments bound to the nylon membrane were detected using a labeled probe. The PCR fragments amplified with specific primers from plasmid pDAB4472 were purified by excising the fragment from agrose gel. The purified DNA fragment were used for making hybridization probes. Hybridization probes were labeled with $^{32}P$ using the random priming kit following manufacturer's instruction, and purified with ProbeQuant™ G-50 micro columns (Amersham/Pharmacia, Piscataway, N.J., USA). A list of probes used for the study is described in Table 7.

Prehybridization and hybridization were carried out at 65° C. for 4 hr and overnight, respectively, using hybridization buffer (Sigma, St. Louis, Mo.). After hybridization, the membrane was washed at 65° C. in washing buffer (10 mM sodium phosphate, 2.5 mM sodium pyrophosphate, 0.5 mM EDTA, 0.1% SDS, pH adjusted to 7.8 with phosphoric acid) for 20 minutes three times. The washed filters were exposed to Phosphorimager screen for autoradiography and images were scanned.

TABLE 7

Location and Length of Probes used in Southern Analysis.

| Probe Name | Genetic Element | Length (bp) |
|---|---|---|
| AtUbi3a | ubiquitin promoter (AtUbi3) | 601 |
| AtUbi3b | ubiquitin promoter (AtUbi3) | 502 |
| AtUbi3c | ubiquitin promoter (AtUbi3) | 601 |
| aad-12 | aad-12 | 671 |

* the mixture of equal amounts of AtUbi3a, AtUbi3b and AtUbi3c was used as probe to detect methylation of aad-12 promoter region Example 6.5

Probe Stripping

DNA probes were stripped off the membrane blots after the Southern hybridization data were obtained, thus the membrane blots could be reused for hybridization with a different DNA probe. Briefly, after exposure, membrane blots were washed in Regeneration Solution 1 (30 mM NaOH, 1 mM $Na_2EDTA$) at room temperature for 10 minutes and in Regeneration Solution 2 (5 mM $NaPO_4$, 1 mM $Na_2EDTA$, 0.1% SDS) at 65° C. for 30 minutes. The membrane blots were then briefly washed in 2×SSC. The membrane blots were exposed to a Phosphorimager screen for autoradiography to ensure all the DNA probes had been stripped before proceeding to the next hybridization.

Example 6.6

Southern Blot Results

Methylation-sensitive restriction enzymes Aci I and Hyp188 III were used to assay potential methylation of the aad-12 gene and its promoter AtUbi3. The expected restriction fragment sizes, which were calculated from the location of subsequent restriction enzyme sites within the T-DNA of pDAB4472, are given in Table 8. Upon methylation of the aad-12 gene or the AtUbi3 promoter the Aci I and Hyp188 III restriction enzyme sites are not cleaved, thereby producing southern blots which detect fragments of a higher molecular weight than expected.

Restriction enzymes Aci I and Hyp188 III were used to examine the aad-12 gene methylation status. Hybridization bands with the expected size were observed using aad-12 as a probe, suggesting no methylation occurred in the recognition site of Aci I and Hyp188 III of aad-12 event pDAB4472-1606. Similarly, bands of the expected molecular weight were detected in DNA samples of event pDAB4472-1606 digested with Hyp188 III using AtUbi3 as a probe, indicating the recognition site was not methylated within the aad-12 promoter sequence.

TABLE 8

Predicted and Observed Hybridizing Fragments in Southern Blot Analysis.

| DNA Probe | Restriction Enzymes | | Expected Fragment Sizes (bp)[1] | Observed Fragment Size (bp)[2] |
|---|---|---|---|---|
| AtUbi3 | Hyp188III | pDAB4472 | 541*, 375, 360, 276, 268, 201, 152, 97, 84 | ~400 and ~250 |
| | | Maverick | none | none |
| | | pDAB4472-1606 | 541, 375, 360, 276, 268, 201, 152, 97, 84 | ~400 and ~250 |

TABLE 8-continued

Predicted and Observed Hybridizing Fragments in Southern Blot Analysis.

| DNA Probe | Restriction Enzymes | | Expected Fragment Sizes (bp)[1] | Observed Fragment Size (bp)[2] |
|---|---|---|---|---|
| aad-12 | Aci I | pDAB4472 | 1646, 424, 138 | Too weak to see |
| | | Maverick | none | none |
| | | pDAB4472-1606 | 1646, 424, 138 | 1646, 424 |
| | Hyp188III | pDAB4472 | 472, 375*, 209*, 23* | Too weak to see |
| | | Maverick | none | none |
| | | pDAB4472-1606 | 472, 375*, 209*, 23* | 472 |

Example 7

Genomic Characterization via Flanking SNP Markers of AAD-12 Soybean Event pDAB4472-1606

To characterize and describe the genomic insertion site, marker sequences located in proximity to the insert were determined. A panel of polymorphic Single Nucleotide Polymorphism (SNP) markers were used to identify and map the transgene location. Soybean event pDAB4472-1606 is located at around 51 cM on chromosome 8. This location is between the two flanking SNP markers BARC-030485-06876 and BARC-038291-07245. More specifically, the location of the transgene was mapped 0.3 cM (~93 kb) away from BARC-030485-06876 (SEQ ID NO:27) and 0.1 cM (~36 kb) away from BARCO38291-07245 (SEQ ID NO:28).

Example 7.1

BLAST with Flanking Border Region Sequences

The flanking border region sequences for soybean event pDAB4472-1606 (see SEQ ID NO:1) were used to BLAST the soybean whole genome sequence. The BLAST results showed that both border sequences of soybean event pDAB4472-1606 were located on chromosome 8 (Gm08).

Example 7.2

SNP Mapping and BLAST Results

Based on results from BLAST with border sequences and mapping, the event was assigned to chromosome 8. As such, SNP markers were selected from the soybean genetic linkage maps. The SNP sequences were selected from SNP markers developed by Dr. Cregan, at the USDA Beltsville Agricultural Research Center. These SNP markers are associated with chromosome 8. The SNP sequences were used to BLAST the soybean whole genome sequence to determine the physical positions of the T-strand insert for soybean event pDAB4472-1606.

Example 8

Agronomic and Yield Field Trial

The agronomic characteristics of soybean event pDAB4472-1606 were compared to an isogenic non-transformed soybean line across diverse geographical locations during the 2009 growing season. Data were collected and analyzed for the following agronomic characteristics:

1.) Stand count: The number of plants in a representative one meter section of each row was counted. Taking data at the VC-V2 growth stage;
2.) Emergence: Calculated by dividing Stand count (above) by number of seeds planted in a one meter section;
3.) Seedling Vigor at V1-V3: Vigor is an overall estimate of the health of the plant. Vigor was rated on a scale of 1 to 10 with 10 being greatest amount of vigor;
4.) Overall visual crop injury, chlorosis and necrosis at 1 day after V3 chemical application;
5.) Overall visual crop injury, chlorosis and necrosis at 7 days after V3 chemical application;
6.) Overall visual crop injury, chlorosis and necrosis at 14 days after V3 chemical application.
7.) Flowering date: Date when ~50% of the plants in each plot have begun to flower. Recorded in the number of days from planting date;
8.) Stand count at R2: The number of plants in a representative one meter section of row were counted. Note taken at the R2 growth stage;
9.) Overall visual crop injury, chlorosis and necrosis at 1 day after R2 chemical application;
10.) Overall visual crop injury, chlorosis and necrosis at 7 days after R2 chemical application;
11.) Overall visual crop injury, chlorosis and necrosis at 14 days after R2 chemical application.
12.) Disease incidence (if any) at R6 growth stage: Recorded the percentage of plants affected by the disease. 0-100% scale;
13.) Insect damage (if any) at R6 growth stage: Recorded the percentage of plant tissue in the plot damaged by insects. 0-100% scale;
14.) Plant height at senescence: Recorded the average height of the plants in each plot. Measured plants from the soil surface to the tip after leaves had fallen. Recorded measurement in centimeters;
15.) Days to maturity. Recorded when 95% of the pods in a plot had reached their dry down color and were at ~15% moisture or less. Recorded in days from planting;
16.) Lodging: Recorded lodging at harvest time. Rated on a scale of 1 to 5. (All plants in a plot standing straight=1 and all plants in the plot flat=5);
17.) Shattering: Recorded shattering at harvest time. Recorded as an estimate of number of pods shattered. 0-100% scale;
18.) Yield: Harvested the entire 2 row plot. Recorded seed weight and moisture. Calculated bu/acre adjusting to 13% moisture; and,
19.) 100 seed weight: For each plot 100 seeds were counted out and recorded weight in grams.

Each trial was set up as a randomized complete block design. Four varieties were planted in each block and each block was replicated 4 times. Each plot was 2 rows wide and the rows were spaced 30 inches apart. Plots were planted on 20 foot centers (total planted length 17.5 ft) with a 2.5 foot alley between plots. In the sprayed section plants that were expected to die were planted in a sub-section to avoid border effect. Field trials which were sprayed were sprayed with two applications of 2,4-D dimethylamine salt at 2240 g ae/ha applied at V3 and R2 growth stages.

Tables 9 and 10 list the results of the study. Table 9 presents the adjusted means from an analysis comparing untransformed Maverick soybean plants and soybean event pDAB4472-1606 in unsprayed conditions. Table 10 presents the adjusted means from an analysis comparing soybean event pDAB4472-1606 sprayed with 2,4-D and soybean event pDAB4472-1606 unsprayed.

TABLE 9

Comparison of Maverick and soybean event pDAB4472-1606.

| Name | 1606 | Maverick |
|---|---|---|
| Emergence | 80 | 79 |
| Seedling vigor at V1 to V3 (1 to 10 scale) | 8.8 | 8.7 |
| Flowering date (days from planting) | 42 | 41 |
| Stand count R1 recalculated | 21.9 | 21.7 |
| Disease incidence if any at R6 (%) | 5.7 | 5.6 |
| Insect damage if any at R6 (%) | 2.2 | 2.2 |
| Plant height at senescence (cm) | 92 | 92 |
| Days to maturity (days from planting) | 129 | 129 |
| Lodging (1 to 5 scale) | 2.0 | 2.1 |
| Shattering (%) | 0.8 | 0.8 |
| Yield (bu/acre)* | 58.3 | 55.3 |
| 100 seed weight (g)* | 15.3 | 15.9 |

*signifies a significant difference (P = 0.05) between 1606 and Maverick.

TABLE 10

Comparison of soybean event pDAB4472-1606 sprayed and unsprayed with 2,4-D.

| Name | 1606 Unsprayed | 1606 Sprayed |
|---|---|---|
| Emergence (%) | 83.3 | 80.2 |
| Seedling vigor at V1 to V3 (1 to 10 scale) | 8.9 | 8.9 |
| Overall crop injury 1 day after V3 spray (%) | 0.0 | 0.3 |
| Overall crop injury 7 days after V3 spray (%) | 0.0 | 2.1 |
| Overall crop injury 14 days after V3 spray (%) | 0.0 | 3.3 |
| Flowering date (days from planting) | 40 | 41 |
| Stand count R1 recalculated | 21 | 21 |
| Overall crop injury 1 day after R2 spray (%) | 0.0 | 3.0 |
| Overall crop injury 7 days after R2 spray (%) | 0.0 | 3.3 |
| Overall crop injury 14 days after R2 spray (%) | 0.0 | 3.1 |
| Disease incidence if any at R6 (%) | 8.9 | 9.1 |
| Insect damage if any at R6 (%) | 2.3 | 2.3 |
| Plant height at senescence (cm) | 84 | 81 |
| Days to maturity (days from planting) | 133 | 133 |
| Lodging (1 to 5 scale) | 1.7 | 1.4 |
| Shattering (%) | 1.2 | 1.2 |
| Yield (bu/acre) | 55.9 | 50.5 |
| 100 seed weight (g) | 15.2 | 15.1 |

Example 9

Use of Soybean Event DAS-1606 Insertion Site for Targeted Integration

Consistent agronomic performance of the transgene of soybean event DAS-1606 over several generations under field conditions suggests that these identified regions around the soybean event DAS-1606 insertion site provide good genomic locations for the targeted integration of other transgenic genes of interest. Such targeted integration overcomes the problems with so-called "position effect," and the risk of creating a mutation in the genome upon integration of the transgene into the host. Further advantages of such targeted integration include, but are not limited to, reducing the large number of transformation events that must be screened and tested before obtaining a transgenic plant that exhibits the desired level of transgene expression without also exhibiting abnormalities resulting from the inadvertent insertion of the transgene into an important locus in the host genome. Moreover, such targeted integration allows for stacking transgenes rendering the breeding of elite plant lines with both genes more efficient.

Using the disclosed teaching, a skilled person is able to target polynucleic acids of interest to the same insertion site on chromosome 8 as that in soybean event DAS-1606 or to a site in close proximity to the insertion site in soybean event DAS-1606. One such method is disclosed in International Patent Application No. WO2008/021207.

Briefly, up to 20 Kb of the genomic sequence flanking 5' to the insertion site and up to 20 Kb of the genomic sequence flanking 3' to the insertion site (see SEQ ID NO:1) are used to flank the gene or genes of interest that are intended to be inserted into a genomic location on chromosome 8 via homologous recombination. The gene or genes of interest can be placed exactly as in the soybean event DAS-1606 insertion site or can be placed anywhere within the 20 Kb regions around the soybean event DAS-1606 insertion sites to confer consistent level of transgene expression without detrimental effects on the plant. The DNA vectors containing the gene or genes of interest and flanking sequences can be delivered into plant cells via one of the several methods known to those skilled in the art, including but not limited to Agrobacterium-mediated transformation. The insertion of the donor DNA vector into the soybean event DAS-1606 target site can be further enhanced by one of the several methods, including but not limited to the co-expression or up-regulation of recombination enhancing genes or down-regulation of endogenous recombination suppression genes. Furthermore, it is known in the art that double-stranded cleavage of specific sequences in the genome can be used to increase homologous recombination frequency, therefore insertion into the soybean event DAS-1606 insertion site and its flanking regions can be enhanced by expression of natural or designed sequence-specific endonucleases for cleaving these sequences. Thus, using the teaching provided herein, any heterologous nucleic acid can be inserted on soybean chromosome 8 at a target site located between a 5' molecular marker (BARC-030485-06876) and a 3' molecular marker (BARC-038291-07245), preferably within SEQ ID NO:1.

Example 10

Excision of the pat Gene Expression Cassette from Soybean Event DAS-1606

The removal of a selectable marker gene expression cassette is advantageous for targeted insertion into the genomic loci of soybean event DAS-1606. The removal of the pat selectable marker from soybean event DAS-1606 allows for the re-use of the pat selectable marker in targeted integration of polynucleic acids into chromosome 8 in subsequent generations of soybean.

Using the disclosed teaching, a skilled person is able to excise polynucleic acids of interest from soybean event DAS-1606. One such method is disclosed in Provisional U.S. Patent Application No. 61/297,628, herein incorporated by reference in its entirety.

Briefly, sequence-specific endonucleases such as zinc finger nucleases are designed which recognize, bind and cleave specific DNA sequences that flank a gene expression cassette. The zinc finger nucleases are delivered into the plant cell by crossing a parent plant which contains transgenic zinc finger nuclease expression cassettes to a second parent plant which contains soybean event DAS-1606. The resulting progeny are grown to maturity and analyzed for the loss of the pat expression cassette via leaf painting with a herbicide which contains glufosinate. Progeny plants which are not resistant to the herbicide are confirmed molecularly and advanced for self-fertilization. The excision and removal of the pat expression cassette is molecularly confirmed in the progeny obtained from the self-fertilization. Using the teaching provided herein, any heterologous nucleic acid can be excised from soybean chromosome 8 at a target site located between a 5' molecular marker (BARC-030485-06876) and a 3' molecular marker (BARC-038291-07245), preferably within SEQ ID NO:1.

The invention claimed is:

1. A transgenic soybean plant or cell comprising a genome, said genome comprising SEQ ID NO:1.

2. A soybean seed comprising a genome comprising Aryloxy Alkanoate Dioxygenase-12 (AAD-12 event pDAB4472-1606 as present in the representative seed deposited with American Type Culture Collection (ATCC) under Accession No. PTA-11028.

3. A soybean seed produced by the plant of claim 1, said seed comprising a genome, said genome comprising SEQ ID NO:1.

4. A soybean plant produced by growing the seed of claim 2, said plant comprising SEQ ID NO:1.

5. A progeny plant of the soybean plant of claim 4, said progeny plant comprising AAD-12 event pDAB4472-1606.

6. A herbicide-tolerant progeny plant of the soybean plant of claim 1, said progeny plant comprising SEQ ID NO:1.

7. A part of the plant of claim 4 wherein said part is selected from the group consisting of pollen, ovule, flowers, shoots, roots, and leaves, said part comprising SEQ ID NO:1.

8. An isolated polynucleotide primer wherein said polynucleotide comprises a nucleotide sequence selected from the group consisting of [SEQ ID NOs: 3-26] SEQ ID NOs: 19 and 20.

9. An isolated polynucleotide comprising SEQ ID NO:1.

10. A method of breeding a soybean plant, said method comprising crossing a first soybean plant of claim 1 with a second soybean plant to produce a third soybean plant comprising a genome, and assaying said third soybean plant for the presence of SEQ ID NO:1 in said genome.

11. A method of introgressing a herbicide tolerance trait into a soybean plant, said method comprising crossing the first soybean plant of claim 1 with a second soybean plant to produce a third soybean plant comprising a genome, and assaying said third soybean plant for presence of SEQ ID NO:1 in said genome.

12. A method of controlling weeds, said method comprising applying an aryloxy alkanoate herbicide to a field, said field comprising a plant of claim 1.

13. The method of claim 12, wherein said herbicide is 2,4-D.

14. The method of claim 12, wherein said method comprises applying a second herbicide to said field.

15. The method of claim 14, wherein said second herbicide is glyphosate.

16. A method of controlling weeds, said method comprising applying an aryloxy alkanoate herbicide to a field, and planting a seed of claim 3 in said field within 14 days of applying the herbicide.

* * * * *

UNITED STATES PATENT AND TRADEMARK OFFICE
CERTIFICATE OF CORRECTION

PATENT NO.         : 8,785,728 B2                                              Page 1 of 1
APPLICATION NO.    : 13/226789
DATED              : July 22, 2014
INVENTOR(S)        : Yunxing Cory Cui et al.

It is certified that error appears in the above-identified patent and that said Letters Patent is hereby corrected as shown below:

In the Claims

In Claim 2, Column 65, line 52, please amend (AAD-12 to (AAD-12).

In Claim 8, Column 66, line 51, delete "SEQ ID NOs: 3-26".

Signed and Sealed this
Thirtieth Day of September, 2014

Michelle K. Lee
*Deputy Director of the United States Patent and Trademark Office*

SEQUENCE LISTING

```
<160> NUMBER OF SEQ ID NOS: 30

<210> SEQ ID NO 1
<211> LENGTH: 11216
<212> TYPE: DNA
<213> ORGANISM: Artificial Sequence
<220> FEATURE:
<223> OTHER INFORMATION: Insert and flanking sequences for soybean Event
      pDAB4472-1606

<400> SEQUENCE: 1
aggtaccgca agatgaagga gcgtctcgtt ggggtttctg aggaaaccac cactggagtt      60
aagaggctct atcagatgca ggcgaatggg actcttctct tccctgctat taatgtcaat     120
gactctgtca ccaagagcaa ggtaatgtct cttttccccc cagatctagt gtcttttttg     180
tgttaaaatg taggattgag ttcggatctg ttgttttgg atgggttttg tgccattggt     240
gaaatgaggt tttgaacctg tcaactgttt gactaatgtc ctctaagaag tctggatcgg     300
tattgggtgc tattttagtg tgtttggatc tgtgtgttga aacgtcagaa cattagtaag     360
ttgcttgcta acgtgacttt aggtaaatgg tcacatgttt tattacacaa ataaggaatt     420
gattctgagt gcacattttg atttgaagct acttttggat aggataaaat aaattatact     480
gaattttact actgttttg gttttaaaat aaaaaaatgt tcaaacataa atcatgttgt     540
ttcaaaatca attttaactc gaaatcgttt tcattccaaa ttggttttgc aaacattgat     600
ccaaaccgag tcttttgtga cgggttgttt attgattagg gtattgaaag taagaagtgg     660
gtgattggat tttgaggaca ttatactagc tggtcatgga tctagttgat tataattgga     720
ttttgctttg ttgcttgtgt tttgtttgtt taaccttta atctgtggtt ttgtaacagt     780
ttgacaactt gtatgggtgc cgtcactctc tccctgatgg tctcatgagg gctaccgatg     840
ttatgattgc tggaaaggtg gctgttgtgg ctggatatgg tgatgttggc aagggttgtg     900
ctgctgcaat gaagcaggct ggtgctcgtg tcatcgtgac cgagattgat cccatctgtg     960
cccttcaggc tctcatggaa ggccttcagg ttctgacctt ggaggatgtt gtttctgagg    1020
ctgatatctt tgtcaccacc accggtaaca aggacatcat catggttgac cacatgagga    1080
aaatgaagaa caatgccatt gtttgcaaca ttggtcactt tgacaatgag atcgacatgc    1140
ttgggctgga gaactacccc ggcgtgaagc gcatcaccat caagcccaa actgacagat    1200 gggtcttccc tgagaccaac accggtatca ttgtcttggc tgagggtcga ttgatgaact    1260
tgggatgcgc cactggacac cccagttttg tgatgtcctg ctccttcacc aaccaggtca    1320
ttgctcagct tgagttgtgg aaggagaaga gtaccggcaa gtacgagaag aaggtttacg    1380
ttttgcccaa gcaccttgat gagaaggtgg ctgcacttca cctgggcaaa cttggagcta    1440
agctgaccca gcttagcaag tcccaggctg attacatcag tgtgcctgtt gagggtccat    1500
acaagcctgc tcactacagg tactaagtga ttgagatgat caactgaaaa gtgagtgagg    1560
gaaagacaaa aatcggtttt atcaatcgga tttgattgtt taattttcct ttttttgatt    1620
tttggtgtta gactttcag atttgtgta gaagaattgt agccattttt atttctgtag    1680
aacttttgtt cgagtgggtg ggaccagtaa ggaggaaggc ggcatcctgt tggtttctgt    1740
```

```
gatatgaaac caatttgggt tgaataaggc ttgttttgtt tgggggatgt gtgcattttg   1800
ctttattaaa tactaaaatt tgtgtttctt tctgccttt caatacatca aagaaaataa    1860
aaaaattcct acccatctat catctagttt cggaaacaca tcgacacatt gtggtattat   1920
ttggtgcttc tgcaatattt ttaagaaagg gcaatcaggg taattaagtt ctccaactaa   1980
tccgatttga gctatatggt gaattaactt aagggtgaa gctctcacaa gttgaatcaa    2040
attcttcacg ttaaactata tttactggag tgtggctagg agtgatgttt ttggccttgg   2100
ttaaactata tttactctcc tttgttaata tggtgtaacc gaggtatact atctttgttg   2160
gacttttatc cactttgtaa ttgattgggg gcacccattt gtgccttta tatatataca    2220 ctatattttc gctgttttaa taaaaaaata aaaattcttt acgttaatct tctcccatct   2280
cgacaatcct tggaagagaa ataagaaaat aagagaatat atttatcttt ttaattcata   2340
gtatttatca taaagtaaaa gtattttaat aaagaaatta tttttaaaaa aattatttga   2400 tttttaaaa agaaattaag aaaaaaaag aagatacaca aaatcatttc caatcatgaa     2460
caatggagaa gaatttccca aatgaaccca cagaatttgt caatttcgtt cttatttctt   2520
tttgaaccaa tcgagtgaaa tgtctccttt ctatttctct ccttaacacc caatccaatt   2580
ataatgttca ggactccttt catagtgaaa aaaaaattgt tcattcttaa aatcaagaga   2640
ttcctatttt gttattaacc tcataaaaca tagctcccaa atagcctatg aaatcgtttg   2700
ctttaatttc tttagttttt gttacaatga taaaacgaat ttagacctcg cccaaattat   2760
aaaacaatat ggtttgttgc ttagaaaaag gaaggaaaa agacaaaagc gactaaggga   2820
taaaaacttc cccatactat atgggtctaa atttagcat gcacattgat ccaatttagg    2880
ctcagagcat tcttgtttca catcaattt tgcaagactc tgtgctggat gattctctgt    2940
ttttgcgtga aaaaatgagt gcaaagttc ctcagtgacg cattggattt gaatatccta    3000
acgtacgtct tgaatgctgt tggtaaagag tggcaacaag aaaaagtcgt attcttcact   3060
agaacatagg tgctcttttt gggtcaacta ttttttattgt gtcactcatc ttcgatgttt   3120
agtcttgcat tgcattgcca ttaattatag cggtgtttgc tgaacggatc ctttatagtg   3180
aattttatgt atctgtcaga gtcagattca atacaagcct tgcaaaattc gctcttagcc   3240
gtacaatatt actcaccgga tcctaaccgg tgtgatcatg ggccgcgatt aaaaatctca    3300
attatatttg gtctaattta gtttggtatt gagtaaaaca aattcgaacc aaaccaaaat   3360
ataaatatat agtttttata tatatgcctt taagactttt tatagaattt tctttaaaaa   3420
atatctagaa atatttgcga ctcttctggc atgtaatatt tcgttaaata tgaagtgctc   3480 cattttatt aactttaaat aattggttgt acgatcactt tcttatcaag tgttactaaa    3540
atgcgtcaat ctctttgttc ttccatattc atatgtcaaa acctatcaaa attcttatat   3600
atctttttcg aatttgaagt gaaatttcga taatttaaaa ttaaatagaa catatcatta   3660
tttaggtatc atattgattt ttatacttaa ttactaaatt tggttaactt tgaaagtgta   3720
catcaacgaa aaattagtca aacgactaaa ataataaat atcatgtgtt attaagaaaa    3780
ttctcctata agaatatttt aatagatcat atgtttgtaa aaaaaattaa tttttactaa   3840
cacatatatt tacttatcaa aaatttgaca aagtaagatt aaaataatat tcatctaaca   3900
aaaaaaaaac cagaaaatgc tgaaaacccg gcaaaaccga accaatccaa accgatatag   3960
ttggtttggt ttgattttga tataaaaccga accaactcgg tccatttgca cccctaatca   4020
taatagcttt aatatttcaa gatattatta agttaacgtt gtcaatatcc tggaaatttt   4080
```

```
gcaaaatgaa tcaagcctat atggctgtaa tatgaattta aaagcagctc gatgtggtgg    4140
taatatgtaa tttacttgat tctaaaaaaa tatcccaagt attaataatt tctgctagga    4200
agaaggttag ctacgattta cagcaaagcc agaatacaat gaaccataaa gtgattgaag    4260
ctcgaaatat acgaaggaac aaatatttt aaaaaaatac gcaatgactt ggaacaaaag     4320
aaagtgatat attttttgtt cttaaacaag catcccctct aaagaatggc agttttcctt    4380
tgcatgtaac tattatgctc ccttcgttac aaaaattttg dactactatt gggaacttct    4440
tctgaaaata gtggccaccg cttaattaag gcgcgccatg cccgggcaag cggccgcaca    4500
agtttgtaca aaaaagcagg ctccgcggaa gcttcggatt tggagccaag tctcataaac    4560
gccattgtgg aagaaagtct tgagttggtg gtaatgtaac agagtagtaa aacagagaa     4620 gagagagagt gtgagataca tgaattgtcg ggcaacaaaa atcctgaaca tcttatttta    4680
gcaaagagaa agagttccga gtctgtagca gaagagtgag gagaaattta agctcttgga    4740
cttgtgaatt gttccgcctc ttgaatactt cttcaatcct catatattct tcttctatgt    4800
tacctgaaaa ccggcattta atctcgcggg tttattccgg ttcaacattt tttttgtttt    4860
gagttattat ctgggcttaa taacgcaggc ctgaaataaa ttcaaggccc aactgttttt    4920
ttttttaaga agttgctgtt aaaaaaaaaa aagggaatta acaacaacaa caaaaaaaga    4980
taaagaaaat aataacaatt actttaattg tagactaaaa aaacatagat tttatcatga    5040 aaaaagaga aagaaataa aaacttggat caaaaaaaa aacatacaga tcttctaatt       5100 attaacttttt cttaaaaatt aggtccttttt tcccaacaat taggtttaga gtttggaat   5160 taaaccaaaa agattgttct aaaaaatact caaatttggt agataagttt ccttattta    5220 attagtcaat ggtagatact tttttttctt ttcttattta gagtagatta gaatcttta    5280 tgccaagtat tgataaatta aatcaagaag ataaactatc ataatcaaca tgaaattaaa    5340
agaaaaatct catatatagt attagtattc tctatatata ttatgattgc ttattcttaa    5400
tgggttgggt taaccaagac atagtcttaa tggaaagaat cttttttgaa cttttccctt   5460
attgattaaa ttcttctata gaaagaaag aaattatttg aggaaaagta tatacaaaaa    5520
gaaaaataga aaaatgtcag tgaagcagat gtaatggatg acctaatcca accaccacca    5580
taggatgttt ctacttgagt cggtctttta aaaacgcacg gtggaaaata tgacacgtat    5640
catatgattc cttcctttag tttcgtgata ataatcctca actgtatatct tcctttttt    5700 gttttggcta aagatatttt attctcatta atagaaaaga cggttttggg cttttggttt   5760
gcgatataaa aagaccttc gtgtggaaga taataattca tcctttcgtc ttttttctgac   5820 tcttcaatct ctcccaaagc ctaaagcgat ctctgcaaat ctctcgcgac tctctctttc    5880
aaggtatatt ttctgattct ttttgttttt gattcgtatc tgatctccaa ttttttgttat   5940 gtggattatt gaatcttttg tataaattgc ttttgacaat attgttcgtt tcgtcaatcc    6000
agcttctaaa ttttgtcctg attactaaga tatcgattcg tagtgtttac atctgtgtaa    6060
tttcttgctt gattgtgaaa ttaggatttt caaggacgat ctattcaatt tttgtgtttt    6120
ctttgttcga ttctctctgt tttaggtttc ttatgtttag atccgtttct ctttggtgtt    6180
gttttgattt ctcttacggc ttttgatttg gtatatgttc gctgattggt ttctacttgt    6240
tctattgttt tatttcagcc atggctcaga ccactctcca aatcacaccc actggtgcca    6300
ccttgggtgc cacagtcact ggtgttcacc ttgccacact tgacgatgct ggtttcgctg    6360
ccctccatga agcctggctt caacatgcac tcttgatctt ccctgggcaa cacctcagca    6420
atgaccaaca gattacccttt gctaaacgct ttggagcaat tgagaggatt ggcggaggtg   6480
```

```
acattgttgc catatccaat gtcaaggcag atggcacagt gcgccagcac tctcctgctg    6540
agtgggatga catgatgaag gtcattgtgg gcaacatggc ctggcacgcc gactcaacct    6600
acatgccagt catggctcaa ggagctgtgt tcagcgcaga agttgtccca gcagttgggg    6660
gcagaacctg ctttgctgac atgagggcag cctacgatgc ccttgatgag caacccgtg    6720 ctcttgttca ccaaaggtct gctcgtcact cccttgtgta ttctcagagc aagttgggac    6780
atgtccaaca ggccgggtca gcctacatag gttatggcat ggacaccact gcaactcctc    6840
tcagaccatt ggtcaaggtg catcctgaga ctggaaggcc cagcctcttg atcggccgcc    6900
atgcccatgc catccctggc atggatgcag ctgaatcaga gcgcttcctt gaaggacttg    6960
ttgactgggc ctgccaggct cccagagtcc atgctcacca atgggctgct ggagatgtgg    7020
ttgtgtggga caaccgctgt tgctccacc gtgctgagcc ctgggatttc aagttgccac    7080
gtgtgatgtg gcactccaga ctcgctggac gcccagaaac tgagggtgct gccttggttt    7140
gagtagttag cttaatcacc tagagctcgg tcaccagcat aattttatt aatgtactaa    7200 attactgttt tgttaaatgc aattttgctt tctcgggatt ttaatatcaa aatctattta    7260
gaaatacaca atattttgtt gcaggcttgc tggagaatcg atctgctatc ataaaaatta    7320
caaaaaaatt ttatttgcct caattatttt aggattggta ttaaggacgc ttaaattatt    7380
tgtcgggtca ctacgcatca ttgtgattga gaagatcagc gatacgaaat attcgtagta    7440
ctatcgataa tttatttgaa aattcataag aaaagcaaac gttacatgaa ttgatgaaac    7500
aatacaaaga cagataaagc cacgcacatt taggatattg ccgagatta ctgaatattg    7560 agtaagatca cggaatttct gacaggagca tgtcttcaat tcagcccaaa tggcagttga    7620
aatactcaaa ccgccccata tgcaggagcg gatcattcat tgtttgtttg gttgcctttg    7680
ccaacatggg agtccaaggt tgcggccgca agggtgggcg cgccgaccca gctttcttgt    7740
acaaagtggt tgcggccgct taattaaatt taaatgcccg ggcgtttaaa cgcggccgct    7800
taattaaggc cggcctgcag caaacccaga aggtaattat ccaagatgta gcatcaagaa    7860
tccaatgttt acgggaaaaa ctatggaagt attatgtaag ctcagcaaga agcagatcaa    7920
tatgcggcac atacgcaacc tatgttcaaa aatgaagaat gtacagatac aagatcctat    7980
actgccagaa tacgaagaag aatacgtaga aattgaaaaa gaagaaccag gcgaagaaaa    8040
gaatcttgaa gacgtaagca ctgacgacaa caatgaaaag aagaagataa ggtcggtgat    8100
tgtgaaagag acatagagga cacatgtaag gtggaaaatg taagggcgga aagtaacctt    8160
atcacaaagg aatcttatcc cccactactt atccttttat attttttccgt gtcattttg    8220 cccttgagtt ttcctatata aggaaccaag ttcggcattt gtgaaaacaa gaaaaaattt    8280
ggtgtaagct attttctttg aagtactgag gatacaactt cagagaaatt tgtaagtttg    8340
tagatctcca tgtctccgga gaggagacca gttgagatta ggccagctac agcagctgat    8400
atggccgcgg tttgtgatat cgttaaccat tacattgaga cgtctacagt gaactttagg    8460
acagagccac aaacaccaca agagtggatt gatgatctag agaggttgca agatagatac    8520
ccttggttgg ttgctgaggt tgagggtgtt gtggctggta ttgcttacgc tgggccctgg    8580
aaggctagga acgcttacga ttggacagtt gagagtactg tttacgtgtc acataggcat    8640
caaaggttgg gcctaggatc cacattgtac acacatttgc ttaagtctat ggaggcgcaa    8700
ggttttaagt ctgtggttgc tgttataggc cttccaaacg atccatctgt taggttgcat    8760
gaggctttgg gatacacagc ccggggtaca ttgcgcgcag ctggatacaa gcatggtgga    8820
```

```
tggcatgatg ttggtttttg gcaaagggat tttgagttgc cagctcctcc aaggccagtt    8880
aggccagtta cccagatctg aggtaccctg agcttgagct tatgagctta tgagcttaga    8940
gctcggatcc actagtaacg gccgccagtg tgctggaatt cgcccttgac tagataggcg    9000
cccagatcgg cggcaatagc ttcttagcgc catcccgggt tgatcctatc tgtgttgaaa    9060
tagttgcggt gggcaaggct ctctttcaga aagacaggcg gccaacggaa cccaaggtga    9120
ggtgggctat ggctctcagt tccttgtgga agcgcttggt ctaaggtgca gaggtgttag    9180
cgggatgaag caaaagtgtc cgattgtaac aagatatgtt gatcctacgt aaggatatta    9240
aagtatgtat tcatcactaa tataatcagt gtattccaat atgtactacg atttccaatg    9300
tctttattgt cgccgtatgt aatcggcgtc acaaataat ccccggtgac tttcttttaa    9360
tccaggatga ataatatgt tattataatt tttgcgattt ggtccgttat aggaattgaa    9420
gtgtgcttgc ggtcgccacc actcccattt cataatttta catgtatttg aaaaataaaa    9480
atttatggta ttcaatttaa acacgtatac ttgtaaagaa tgatatcttg aaagaaatat    9540
agtttaaata tttattgata aaataacaag tcaggtatta tagtccaagc aaaaacataa    9600
atttattgat gcaagtttaa attcagaaat atttcaataa ctgattatat cagctggtac    9660
attgccgtag atgaaagact gagtgcgata ttatggtgta acatagcg gccgggtttc      9720 tagtcaccgg ttaggatccg tttaaactcg aggctagcgc atgcacatag acacacacat    9780
catctcattg atgcttggta ataattgtca ttagattgtt tttatgcata gatgcactcg    9840
aaatcagcca attttagaca agtatcaaac ggatgtgact tcagtacatt aaaaacgtcc    9900
gcaatgtgtt attaagttgt ctaagcgtca atttgattta caattgaact tctcaatact    9960
gatctggaaa aggacaagag gccaataaca caatttgcat ctcgaatacg ccaattgtat    10020
ttttatacgc agcctcattc atagtccatt agtcaaagta tgtggtttga aaacaggaat    10080
aacgaaaacc aagtatgaga gtgctagtaa agattgattg agtaacaagt cactattgag    10140
atgtttccaa aaacgtcaac gacaaataaa caatttgat aaaagtttca tgatattttc     10200 cctaatatt tattaagaat cttgaataag ctaatgttag gtgtgaaaat aagcatgaac     10260
aacttggata ttaatagacc aacaaagtaa aaaggtccta tcttgcttag tccccaatcc    10320 tcaataaaata atacagtaga aaggataaaa ctactggaaa tccttctata taattatgaa    10380
gtatcacatt caataaatct tgataacatt aaatgcatca aaaataaaag ataggaattt    10440
caaggttttg aaagttcatc tttaactctg atatcacatt cattttataa agatcgagat    10500
aacattttta aggattcttg aaaatatgaa aattaattta tttctattta ttactttcgg    10560
gtgaaattat accccttaac tatataaatg aaaacttgtg atgagttgta gcaaacaagt    10620
gagatgcttt taagagtgag agagtttttg taattctctt caataaaaga gagttatatt    10680
tcattatact tggtgagtgt ttgagaaata ttttaaatca tcatattgag tgagattaaa    10740
atcattgtaa tcctatttca tagtgaagat atttttttttg acttgatttc gtgatttttt    10800
cctttcacat taaattttt ttggtattat tcttcttctc ttattctctt agtttatttt      10860
tcttatcatt catcttaatg atataaagtg ggaaatttat tcttgatatt ttccaacaaa    10920
aataaagcag gttatcaatc ccattactaa acaagtccaa agttggtggg ttgcgggtgg    10980
taggtgtgtt aaacgtgttc gacaaatctt taaattacga tctcaattct ctactgccga    11040
aggtgtgacc tcacatacat ctttgtatac tattaataaa taataaattt atgcgaaaat    11100
gatgttgtta tggcattatt ttatgtcaag acaaaaacat gaaatgtgga gtatctgcca    11160
tttggttctc tctaattatt gtttgaaata gtggttttca tagaatcatc attcag        11216
```

```
<210> SEQ ID NO 2
<211> LENGTH: 24
<212> TYPE: DNA
<213> ORGANISM: Artificial Sequence
<220> FEATURE:
<223> OTHER INFORMATION: Primer ES_LEnd03

<400> SEQUENCE: 2
tggaagaaca aagagattga cgca                                            24

<210> SEQ ID NO 3
<211> LENGTH: 21
<212> TYPE: DNA
<213> ORGANISM: Artificial Sequence
<220> FEATURE:
<223> OTHER INFORMATION: Primer ES_PATEnd_02

<400> SEQUENCE: 3
ggtggatggc atgatgttgg t                                               21

<210> SEQ ID NO 4
<211> LENGTH: 28
<212> TYPE: DNA
<213> ORGANISM: Artificial Sequence
<220> FEATURE:
<223> OTHER INFORMATION: Primer ES_LEnd04

<400> SEQUENCE: 4
acgaaatatt acatgccaga agagtcgc                                        28

<210> SEQ ID NO 5
<211> LENGTH: 22
<212> TYPE: DNA
<213> ORGANISM: Artificial Sequence
<220> FEATURE:
<223> OTHER INFORMATION: Primer ES_PATEnd_01

<400> SEQUENCE: 5
ccagctcctc caaggccagt ta                                              22

<210> SEQ ID NO 6
<211> LENGTH: 24
<212> TYPE: DNA
<213> ORGANISM: Artificial Sequence
<220> FEATURE:
<223> OTHER INFORMATION: Primer ES_PATEnd03

<400> SEQUENCE: 6
ccgtagatga aagactgagt gcga                                            24

<210> SEQ ID NO 7
<211> LENGTH: 30
<212> TYPE: DNA
<213> ORGANISM: Artificial Sequence
<220> FEATURE:
<223> OTHER INFORMATION: Primer ES_PATEnd04

<400> SEQUENCE: 7
ccgtagatga aagactgagt gcgatattat                                      30

<210> SEQ ID NO 8
<211> LENGTH: 19
<212> TYPE: DNA
<213> ORGANISM: Artificial Sequence
<220> FEATURE:
```

<223> OTHER INFORMATION: Primer 56LEndG01

<400> SEQUENCE: 8
tgtttgctga acggatcct                                              19

<210> SEQ ID NO 9
<211> LENGTH: 22
<212> TYPE: DNA
<213> ORGANISM: Artificial Sequence
<220> FEATURE:
<223> OTHER INFORMATION: Primer 56LEndG02

<400> SEQUENCE: 9
tggtaaagag tggcaacaag aa                                          22

<210> SEQ ID NO 10
<211> LENGTH: 20
<212> TYPE: DNA
<213> ORGANISM: Artificial Sequence
<220> FEATURE:
<223> OTHER INFORMATION: Primer 56LendG03

<400> SEQUENCE: 10
gtgggaccag taaggaggaa                                             20

<210> SEQ ID NO 11
<211> LENGTH: 22
<212> TYPE: DNA
<213> ORGANISM: Artificial Sequence
<220> FEATURE:
<223> OTHER INFORMATION: Primer 56LendG04

<400> SEQUENCE: 11
aaagtgagtg agggaaagac aa                                          22

<210> SEQ ID NO 12
<211> LENGTH: 22
<212> TYPE: DNA
<213> ORGANISM: Artificial Sequence
<220> FEATURE:
<223> OTHER INFORMATION: Primer 56PATG01

<400> SEQUENCE: 12
tattgaggat tggggactaa gc                                          22

<210> SEQ ID NO 13
<211> LENGTH: 25
<212> TYPE: DNA
<213> ORGANISM: Artificial Sequence
<220> FEATURE:
<223> OTHER INFORMATION: Primer 56PATG02

<400> SEQUENCE: 13
ttgactaatg gactatgaat gaggc                                       25

<210> SEQ ID NO 14
<211> LENGTH: 23
<212> TYPE: DNA
<213> ORGANISM: Artificial Sequence
<220> FEATURE:
<223> OTHER INFORMATION: Primer 56PATG03

<400> SEQUENCE: 14
ggcagatact ccacatttca tgt                                         23

```
<210> SEQ ID NO 15
<211> LENGTH: 20
<212> TYPE: DNA
<213> ORGANISM: Artificial Sequence
<220> FEATURE:
<223> OTHER INFORMATION: Primer 56PATG05

<400> SEQUENCE: 15
ccaaatggca gatactccac                                               20

<210> SEQ ID NO 16
<211> LENGTH: 17
<212> TYPE: DNA
<213> ORGANISM: Artificial Sequence
<220> FEATURE:
<223> OTHER INFORMATION: Primer AIILEnd05

<400> SEQUENCE: 16
gtgttgccca gggaaga                                                  17

<210> SEQ ID NO 17
<211> LENGTH: 20
<212> TYPE: DNA
<213> ORGANISM: Artificial Sequence
<220> FEATURE:
<223> OTHER INFORMATION: Primer PAT-End05

<400> SEQUENCE: 17
gctcctccaa ggccagttag                                               20

<210> SEQ ID NO 18
<211> LENGTH: 20
<212> TYPE: DNA
<213> ORGANISM: Artificial Sequence
<220> FEATURE:
<223> OTHER INFORMATION: Primer PAT-End06

<400> SEQUENCE: 18
ccagttaggc cagttaccca                                               20

<210> SEQ ID NO 19
<211> LENGTH: 25
<212> TYPE: DNA
<213> ORGANISM: Artificial Sequence
<220> FEATURE:
<223> OTHER INFORMATION: Primer Soy1606-F

<400> SEQUENCE: 19
cggttaggat ccggtgagta atatt                                         25

<210> SEQ ID NO 20
<211> LENGTH: 24
<212> TYPE: DNA
<213> ORGANISM: Artificial Sequence
<220> FEATURE:
<223> OTHER INFORMATION: Primer Soy1606-R

<400> SEQUENCE: 20
gccattaatt atagcggtgt ttgc                                          24

<210> SEQ ID NO 21
<211> LENGTH: 13
<212> TYPE: DNA
<213> ORGANISM: Artificial Sequence
<220> FEATURE:
<223> OTHER INFORMATION: Prober Soy1606-Probe
```

<400> SEQUENCE: 21
ccttgcaaaa ttc                                                          13

<210> SEQ ID NO 22
<211> LENGTH: 20
<212> TYPE: DNA
<213> ORGANISM: Artificial Sequence
<220> FEATURE:
<223> OTHER INFORMATION: Primer ZN_007

<400> SEQUENCE: 22
tcccgagtgg gtgaggatag                                                   20

<210> SEQ ID NO 23
<211> LENGTH: 20
<212> TYPE: DNA
<213> ORGANISM: Artificial Sequence
<220> FEATURE:
<223> OTHER INFORMATION: Primer ZN_008

<400> SEQUENCE: 23
tcatgcgatt ccccaggtat                                                   20

<210> SEQ ID NO 24
<211> LENGTH: 23
<212> TYPE: DNA
<213> ORGANISM: Artificial Sequence
<220> FEATURE:
<223> OTHER INFORMATION: Probe ZN_LT_002

<400> SEQUENCE: 24
ttctctgctg ccacgggact cga                                               23

<210> SEQ ID NO 25
<211> LENGTH: 25
<212> TYPE: DNA
<213> ORGANISM: Artificial Sequence
<220> FEATURE:
<223> OTHER INFORMATION: Primer Soy1606-F - TaqMan

<400> SEQUENCE: 25
cggttaggat ccggtgagta atatt                                             25

<210> SEQ ID NO 26
<211> LENGTH: 24
<212> TYPE: DNA
<213> ORGANISM: Artificial Sequence
<220> FEATURE:
<223> OTHER INFORMATION: Primer Soy1606-R - TaqMan

<400> SEQUENCE: 26
gccattaatt atagcggtgt ttgc                                              24

<210> SEQ ID NO 27
<211> LENGTH: 351
<212> TYPE: DNA
<213> ORGANISM: Artificial Sequence
<220> FEATURE:
<223> OTHER INFORMATION: BARC-030485-06876 is a 5' Marker at Chromosome
      8 of Glycine Max soybean event pDAB4472-1606

<400> SEQUENCE: 27
ctgatattca gttttccagg ctaagctgag atatatttta tatccctctt aaaaacaatt       60
ccaagatgag aggatatctg ctttgaccct tcaattgcag gattatccgc caggttgaat      120

```
gacttctttt tcaacatgaa ccgcaaacgt aaccgttggt ggctgcaagc tctgcacaaa      180
caagttgaaa taaacagtt caaatcggag gaaccaatta tgggtattac atataacata       240
atcatggttc atgcacatac cgttattctg caatgaatat aagatcatc gtgcatctga      300 ctaagacggt tctttgcaag ttcttcagct gcacatgctt tcctgcaagc t              351
```

<210> SEQ ID NO 28
<211> LENGTH: 545
<212> TYPE: DNA
<213> ORGANISM: Artificial Sequence
<220> FEATURE:
<223> OTHER INFORMATION: BARC-038291-07245 is a 3' Marker at Chromosome
      8 of Soybean Event pDAB4472-1606

<400> SEQUENCE: 28

```
aatgaagcta tagcttgcag caaattaaag aatgaaagta attaaggagt agctaggcac       60
gaaagaaaag ggtatgaggg tgggaatgaa tgtggcaaag tggctcagat atatatatac      120
atgcataatt gaaagggtg gtaggtaga tgcgcgcatg cttcctctga ctacgctttt       180
ttttctttca aatatatggt gtatgtaccg catgtctaag tagactgttg actctcccaa      240
cacaccaacc cattcttttc ccccaataat cagcaawttt ttttttttgtt ctccatagtc     300 catacttctt tacaattgct tctcctaatt ttggaattac ttttttatt tctggtttta     360 aaagagtttt tggaaaaata attactyact gttatgtgtg ttgatgtgaa tgaaagggac      420
tcatatccct ggtaagaaat tagttttgat cagtttcaag tgtatcaaaa agaaatgtca     480
cgagagattt acttgttta atattgtgcg taaatgatta gtttaagttc atttatcgcc      540
caaaa                                                                 545
```

<210> SEQ ID NO 29
<211> LENGTH: 3224
<212> TYPE: DNA
<213> ORGANISM: Artificial Sequence
<220> FEATURE:
<223> OTHER INFORMATION: 5' flanking sequence in soybean event pDAB4472-
      1606

<400> SEQUENCE: 29

```
aggtaccgca agatgaagga gcgtctcgtt gggtttctg aggaaaccac cactggagtt        60
aagaggctct atcagatgca ggcgaatggg actcttctct tccctgctat taatgtcaat     120
gactctgtca ccaagagcaa ggtaatgtct cttttttccc cagatctagt gtcttttttg     180
tgttaaaatg taggattgag ttcggatctg ttgttttgg atgggttttg tgccattggt     240
gaaatgaggt tttgaacctg tcaactgttt gactaatgtc ctctaagaag tctggatcgg      300
tattgggtgc tattttagtg tgtttggatc tgtgtgttga aacgtcagaa cattagtaag     360
ttgcttgcta acgtgacttt aggtaaatgg tcacatgttt tattacacaa ataaggaatt     420
gattctgagt gcacattttg atttgaagct acttttggat aggataaaat aaattatact    480
gaattttact actgttttg gttttaaaat aaaaaatgt tcaaacataa atcatgttgt      540
ttcaaaatca attttaactc gaaatcgttt tcattcaaaa ttggtttgc aaacattgat     600 ccaaaccgag tcttttgtga cgggttgttt attgattagg gtattgaaag taagaagtgg      660
gtgattggat tttgaggaca ttatactagc tggtcatgga tctagttgat tataattgga    720
ttttgctttg ttgcttgtgt tttgtttgtt taaccttta atctgtggtt ttgtaacagt     780
ttgacaactt gtatgggtgc cgtcactctc tccctgatgg tctcatgagg gctaccgatg     840
ttatgattgc tggaaaggtg gctgttgtgg ctggatatgg tgatgttggc aagggttgtg      900
```

```
ctgctgcaat gaagcaggct ggtgctcgtg tcatcgtgac cgagattgat cccatctgtg    960
cccttcaggc tctcatggaa ggccttcagg ttctgacctt ggaggatgtt gtttctgagg   1020
ctgatatctt tgtcaccacc accggtaaca aggacatcat catggttgac cacatgagga   1080
aaatgaagaa caatgccatt gtttgcaaca ttggtcactt tgacaatgag atcgacatgc   1140
ttgggctgga gaactacccc ggcgtgaagc gcatcaccat caagcccaa actgacagat    1200 gggtcttccc tgagaccaac accggtatca ttgtcttggc tgagggtcga ttgatgaact   1260
tgggatgcgc cactggacac cccagttttg tgatgtcctg ctccttcacc aaccaggtca   1320
ttgctcagct tgagttgtgg aaggagaaga gtaccggcaa gtacgagaag aaggtttacg   1380
ttttgcccaa gcaccttgat gagaaggtgg ctgcacttca cctgggcaaa cttggagcta   1440
agctgaccca gcttagcaag tcccaggctg attacatcag tgtgcctgtt gagggtccat   1500
acaagcctgc tcactacagg tactaagtga ttgagatgat caactgaaaa gtgagtgagg   1560
gaaagacaaa aatcggtttt atcaatcgga tttgattgtt taattttcct tttttgatt    1620 tttggtgtta gacttttcag atttgtggta gaagaattgt agccattttt atttctgtag   1680
aacttttgtt cgagtgggtg ggaccagtaa ggaggaaggc ggcatcctgt tggtttctgt   1740
gatatgaaac caatttgggt tgaataaggc ttgttttgtt tgggggatgt gtgcattttg   1800
ctttattaaa tactaaaatt tgtgtttctt tctgcctttt caatacatca agaaaataa    1860 aaaaattcct acccatctat catctagttt cggaaacaca tcgacacatt gtggtattat   1920
ttggtgcttc tgcaatattt ttaagaaagg gcaatcaggg taattaagtt ctccaactaa   1980
tccgatttga gctatatggt gaattaactt aaggggtgaa gctctcacaa gttgaatcaa   2040
attcttcacg ttaaactata tttactggag tgtggctagg agtgatgttt ttggccttgg   2100
ttaaactata tttactctcc tttgttaata tggtgtaacc gaggtatact atctttgttg   2160 gactttatc cactttgtaa ttgattgggg gcacccattt gtgccttta tatatataca     2220 ctatattttc gctgttttaa taaaaaaata aaaattcttt acgttaatct tctcccatct   2280
cgacaatcct tggaagagaa ataagaaaat aagagaatat atttatcttt ttaattcata   2340
gtatttatca taaagtaaaa gtatttaat aaagaaatta tttttaaaaa aattatttga    2400
ttttttaaaa agaaattaag aaaaaaaaag aagatacaca aaatcatttc caatcatgaa   2460
caatggagaa gaatttccca aatgaaccca cagaatttgt caatttcgtt cttatttctt   2520
tttgaaccaa tcgagtgaaa tgtctccttt ctatttctct ccttaacacc caatccaatt   2580
ataatgttca ggactccttt catagtgaaa aaaaattgt tcattcttaa aatcaagaga    2640
ttcctatttt gttattaacc tcataaaaca tagctcccaa atagcctatg aaatcgtttg   2700
ctttaatttc tttagttttt gttacaatga taaaacgaat ttagacctcg cccaaaattat  2760 aaaacaatat ggtttgttgc ttagaaaaag gaaggaaaa agacaaaagc gactaaggga   2820
taaaaacttc cccatactat atgggtctaa attttagcat gcacattgat ccaatttagg   2880
ctcagagcat tcttgtttca catcaatttt tgcaagactc tgtgctggat gattctctgt   2940
ttttgcgtga aaaatgagt gcaaaagttc ctcagtgacg cattggattt gaatatccta    3000
acgtacgtct tgaatgctgt tggtaaagag tggcaacaag aaaaagtcgt attcttcact   3060
agaacatagg tgctcttttt gggtcaacta ttttattgt gtcactcatc ttcgatgttt    3120
agtcttgcat tgcattgcca ttaattatag cggtgtttgc tgaacggatc ctttatagtg   3180 aatttatgt atctgtcaga gtcagattca atacaagcct tgca                     3224
```

```
<210> SEQ ID NO 30
<211> LENGTH: 1268
<212> TYPE: DNA
<213> ORGANISM: Artificial Sequence
<220> FEATURE:
<223> OTHER INFORMATION: 3' flanking sequence in soybean event pDAB4472-
      1606

<400> SEQUENCE: 30
cttctcaata ctgatctgga aaaggacaag aggccaataa cacaatttgc atctcgaata     60
cgccaattgt atttttatac gcagcctcat tcatagtcca ttagtcaaag tatgtggttt    120
gaaaacagga ataacgaaaa ccaagtatga gagtgctagt aaagattgat tgagtaacaa    180
gtcactattg agatgtttcc aaaaacgtca acgacaaata aacaattttg ataaaagttt    240
catgatattt tccctaatat tttattaaga atcttgaata agctaatgtt aggtgtgaaa    300
ataagcatga acaacttgga tattaataga ccaacaaagt aaaaaggtcc tatcttgctt    360
agtccccaat cctcaataaa taatacagta gaaaggataa aactactgga aatccttcta    420
tataattatg aagtatcaca ttcaataaat cttgataaca ttaaatgcat caaaaataaa    480
agataggaat ttcaaggttt tgaaagttca tctttaactc tgatatcaca ttcattttat    540
aaagatcgag ataacatttt taaggattct tgaaaatatg aaaattaatt tatttctatt    600
tattactttc gggtgaaatt ataccccttta actatataaa tgaaaacttg tgatgagttg    660
tagcaaacaa gtgagatgct tttaagagtg agagagtttt tgtaattctc ttcaataaaa    720
gagagttata tttcattata cttggtgagt gtttgagaaa tattttaaat catcatattg    780
agtgagatta aaatcattgt aatcctattt catagtgaag atatttttt tgacttgatt    840 tcgtgatttt ttcctttcac attaaatttt ttttggtatt attcttcttc tcttattctc    900
ttagtttatt tttcttatca ttcatcttaa tgatataaag tgggaaattt attcttgata    960
ttttccaaca aaataaagc aggttatcaa tcccattact aaacaagtcc aaagttggtg   1020
ggttgcgggt ggtaggtgtg ttaaacgtgt tcgacaaatc tttaaattac gatctcaatt   1080
ctctactgcc gaaggtgtga cctcacatac atctttgtat actattaata aataataaat   1140
ttatgcgaaa atgatgttgt tatggcatta ttttatgtca agacaaaaac atgaaatgtg   1200
gagtatctgc catttggttc tctctaatta ttgtttgaaa tagtggtttt catagaatca   1260
tcattcag                                                           1268
```